US011806076B2

(12) United States Patent
Ono et al.

(10) Patent No.: US 11,806,076 B2
(45) Date of Patent: *Nov. 7, 2023

(54) OPHTHALMOLOGIC APPARATUS, AND METHOD OF CONTROLLING THE SAME

(71) Applicant: Topcon Corporation, Tokyo (JP)

(72) Inventors: Yusuke Ono, Kita-ku (JP); Hiroyuki Aoki, Saitama (JP)

(73) Assignee: TOPCON CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/891,140

(22) Filed: Aug. 19, 2022

(65) Prior Publication Data
US 2022/0386869 A1 Dec. 8, 2022

Related U.S. Application Data

(63) Continuation of application No. 16/739,137, filed on Jan. 10, 2020, now Pat. No. 11,452,445.

(30) Foreign Application Priority Data

Jan. 24, 2019 (JP) ................. 2019-009865

(51) Int. Cl.
A61B 3/00 (2006.01)
A61B 3/10 (2006.01)
(Continued)

(52) U.S. Cl.
CPC ............ *A61B 3/0025* (2013.01); *A61B 3/102* (2013.01); *A61B 3/12* (2013.01); *A61B 3/14* (2013.01);
(Continued)

(58) Field of Classification Search
CPC ......... A61B 3/0025; A61B 3/102; A61B 3/12; A61B 3/14; A61B 3/1241; G06V 10/143;
(Continued)

(56) References Cited

U.S. PATENT DOCUMENTS 9,161,690 B2 * 10/2015 Tomatsu ................ A61B 3/113
11,452,445 B2 * 9/2022 Ono ..................... G06V 10/751
(Continued)

FOREIGN PATENT DOCUMENTS

CN 107292868 A 10/2017
JP 2010-279536 A 12/2010
(Continued)

OTHER PUBLICATIONS

Partial European Search Report dated Jul. 3, 2020 in European Application No. 19219997.4.
(Continued)

*Primary Examiner* — Mohammed A Hasan
(74) *Attorney, Agent, or Firm* — XSENSUS LLP

(57) ABSTRACT

An ophthalmologic apparatus of an embodiment example includes a front image acquiring device, a first search processor, and a second search processor. The front image acquiring device is configured to acquire a front image of a fundus of a subject's eye. The first search processor is configured to search for an interested region corresponding to an interested site of the fundus based on a brightness variation in the front image. The second search processor is configured to search for the interested region by template matching between the front image and a template image in the event that the interested region has not been detected by the first search processor.

15 Claims, 18 Drawing Sheets

(51) Int. Cl.

| | |
|---|---|
| *A61B 3/12* | (2006.01) |
| *A61B 3/14* | (2006.01) |
| *G06V 10/25* | (2022.01) |
| *G06V 10/75* | (2022.01) |
| *G06V 10/80* | (2022.01) |
| *G06V 10/143* | (2022.01) |
| *G06V 10/147* | (2022.01) |
| *G06V 40/19* | (2022.01) |
| *G06V 40/18* | (2022.01) |
| *G06V 40/14* | (2022.01) |

(52) U.S. Cl.
CPC .......... *G06V 10/143* (2022.01); *G06V 10/147* (2022.01); *G06V 10/25* (2022.01); *G06V 10/751* (2022.01); *G06V 10/803* (2022.01); *G06V 10/809* (2022.01); *G06V 40/19* (2022.01); *G06V 40/193* (2022.01); *G06V 40/14* (2022.01)

(58) Field of Classification Search
CPC .... G06V 10/147; G06V 10/25; G06V 10/751; G06V 10/803; G06V 10/809; G06V 40/19; G06V 40/193; G06V 40/14; G06F 18/251; G06F 18/254
USPC ........................................................ 351/206
See application file for complete search history.

(56) References Cited

U.S. PATENT DOCUMENTS

| | | | |
|---|---|---|---|
| 2009/0190093 A1 | 7/2009 | Tanassi et al. | |
| 2010/0149489 A1 | 6/2010 | Kikawa et al. | |
| 2012/0002166 A1 | 1/2012 | Tomatsu et al. | |
| 2012/0157820 A1 | 6/2012 | Zhang et al. | |
| 2013/0063698 A1 | 3/2013 | Akiba et al. | |
| 2013/0301008 A1 | 11/2013 | Srivastava et al. | |
| 2014/0198300 A1* | 7/2014 | Goto ................. | G01B 9/02044 351/246 |
| 2014/0268046 A1 | 9/2014 | Narasimha-Iyer et al. | |
| 2014/0276025 A1 | 9/2014 | Durbin et al. | |
| 2015/0313467 A1 | 11/2015 | Sakai et al. | |
| 2016/0157710 A1 | 6/2016 | Tomatsu et al. | |
| 2016/0317029 A1 | 11/2016 | Srivastava et al. | |
| 2017/0042422 A1 | 2/2017 | Sakai et al. | |

FOREIGN PATENT DOCUMENTS

| | | |
|---|---|---|
| JP | 2012-30054 A | 2/2012 |
| JP | 4971872 B2 | 7/2012 |
| JP | 2013-59551 A | 4/2013 |
| JP | 2014-128620 A | 7/2014 |
| JP | 2015-515894 A | 6/2015 |
| JP | 2016-43155 A | 4/2016 |
| JP | 2016-509914 A | 4/2016 |
| JP | 2018-685 A | 1/2018 |
| JP | 2018-23816 A | 2/2018 |

OTHER PUBLICATIONS

Rashid Jalal Qureshi et al: "Combining algorithms for automatic detection of optic disc and macula in fundus images", Computer Vision and Image Understanding, Academic Press, US, vol. 116, No. 1, Sep. 1, 2011 (Sep. 1, 2011), pp. 138-145, XP028112808, ISSN: 1077-3142, DOI: 10.1016/J.CVIU.2011.09.001 [retrieved on Sep. 16, 2011].
Daugman J: "Biometric Decision Landscapes", Technical Report—University of Cambridge. Computer Laboratory, XX, XX, Jan. 1, 2000 (Jan. 1, 2000), pp. 1-13, XP001221883.
Eric Granger et al: "Fusion of biometric systems using Boolean combination: an application to iris-based authentication", International Journal of Biometrics, vol. 4, No. 3, Jul. 31, 2012 (Jul. 31, 2012), pp. 291-315, XP55707011, GB ISSN: 1755-8301, DOI: 10.1504/IJBM.2012.047645.
Extended European search report dated Feb. 8, 2021, in corresponding European patent Application No. 20198738.5, 14 pages.
Extended European search report dated Feb. 11, 2021, in corresponding European patent Application No. 20198735.1, 13 pages.
Zhang et al., "Handbook of Multibiometrics, International Series on Biometrics", Handbook of Multibiometrics, Springer, pp. 4, 5, and 44-65, total 26 pages.
Cao et al., "Automated Control Point Detection, Registration, and Fusion of Fuzzy Retinal Vasculature Images", 2008 IEEE International Conference on Fuzzy Systems {FUZZ 2008), pp. 2386-2391.
Hervella et al., "Multimodal Registration of Retinal Images Using Domain-Specific Landmarks and Vessel Ehancement", total 11 pages.
Zana et al., "A Multimodal Registration Algorithm of Eye Fundus Images Using Vessels Detection and Hough Transform", IEEE Transactions on Medical Imaging, vol. 18, No. 5, May 1999, pp. 419-428.
Bashir et al., "Eagle-Eyes™: A System for Iris Recognition at a Distance", 2008, IEEE, pp. 426-431.
Doynov et al., "A Standoff System for Noncooperative Ocular Biometrics", 2012, IEEE, pp. 144-149.
Office Action dated Jul. 26, 2022, in corresponding Japanese patent Application No. 2019-009865, 8 pages.
Office Action dated Jun. 10, 2022, in corresponding European patent Application No. 19219997.4, 6 pages.
Takao Murakami et al., "Optimal sequential fusion for multibiometric cryptosystems", Information Fusion, Elsevier, vol. 32, 2016, pp. 93-108.
European Office Action dated Feb. 13, 2023 in corresponding European Patent Application No. 20198735.1, 6 pages.
European Office Action dated Jan. 31, 2023, in corresponding European Patent Application No. 20198738.5, 6 pages.
European Office Action dated Jul. 13, 2023, in corresponding European Patent Application No. 20198735.1, 5pp.
Japanese Office Action dated May 30, 2023, in corresponding Japanese Patent Application No. 2022-135078, 6pp.

* cited by examiner

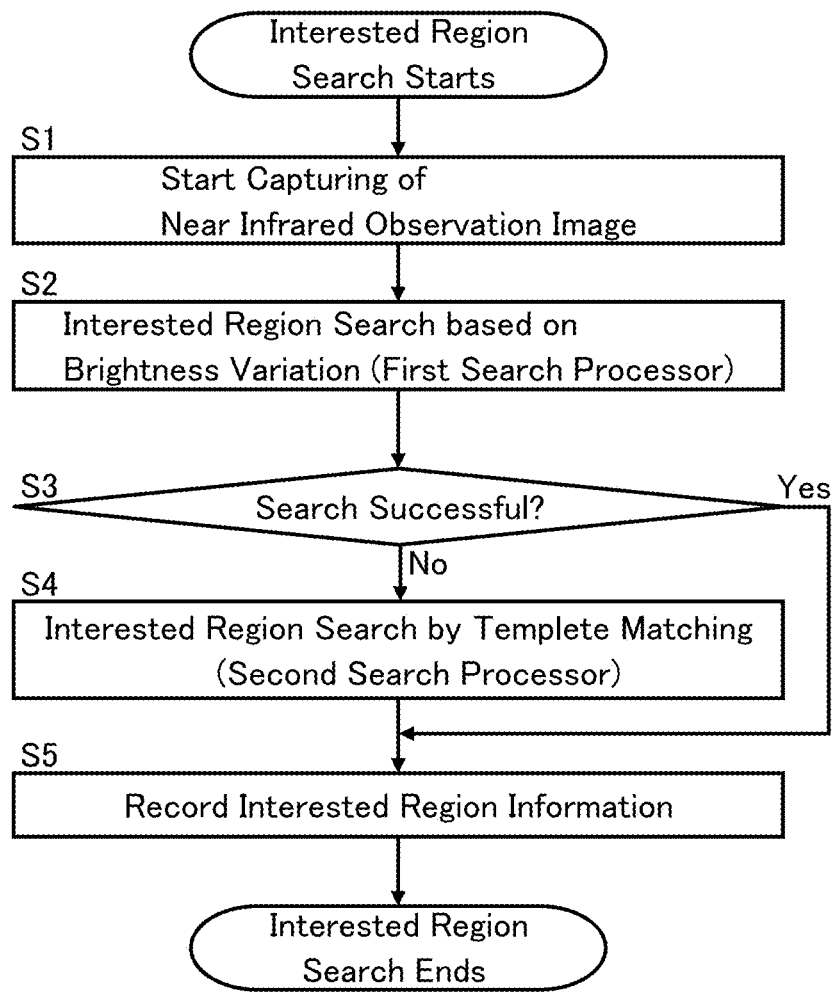

OPHTHALMOLOGIC APPARATUS, AND METHOD OF CONTROLLING THE SAME

CROSS-REFERENCE TO RELATED APPLICATIONS

The present application is a continuation of U.S. application Ser. No. 16/739,137, filed Jan. 10, 2020, which claims priority to Japanese Patent Application No. 2019-009865, filed Jan. 24, 2019 entitled "OPHTHALMOLOGIC APPARATUS, METHOD OF CONTROLLING THE SAME, PROGRAM, AND RECORDING MEDIUM", the entirety of which is incorporated herein by reference.

FIELD

The present disclosure relates to an ophthalmologic apparatus, and a method of controlling the same.

BACKGROUND

In ophthalmologic practice, there are cases in which an examination is performed on a site of interest (or interested site) of the eye and its surroundings. In such cases, the location and area of the targeted interested site should be identified accurately before data acquisition. A typical example of the interested site is the optic nerve head. Japanese Patent No. 4971872 discloses a technique capable of appropriately detecting an interested site even from a relatively low-quality fundus image obtained by near infrared imaging.

BRIEF SUMMARY

An object of the present invention is to improve the reliability of detection of an interested site of an eye fundus.

The first aspect of embodiment examples is an ophthalmologic apparatus comprising: a front image acquiring device configured to acquire a front image of a fundus of a subject's eye; a first search processor configured to search for an interested region corresponding to an interested site of the fundus based on a brightness variation in the front image; and a second search processor configured to search for the interested region by template matching between the front image and a template image in the event that the interested region has not been detected by the first search processor.

The second aspect of embodiment examples is the ophthalmologic apparatus of the first aspect, further comprising a third search processor configured to detect a blood vessel region corresponding to a blood vessel of the fundus by analyzing the front image and search for the interested region based on a distribution of the blood vessel region in the event that the interested region has not been detected by the second search processor.

The third aspect of embodiment examples is an ophthalmologic apparatus comprising: a front image acquiring device configured to acquire a front image of a fundus of a subject's eye; a second search processor configured to search for an interested region by template matching between the front image and a template image; and a third search processor configured to detect a blood vessel region corresponding to a blood vessel of the fundus by analyzing the front image and search for the interested region based on a distribution of the blood vessel region in the event that the interested region has not been detected by the second search processor.

The fourth aspect of embodiment examples is an ophthalmologic apparatus comprising: a front image acquiring device configured to acquire a front image of a fundus of a subject's eye; a first search processor configured to search for an interested region corresponding to an interested site of the fundus based on a brightness variation in the front image; and a third search processor configured to detect a blood vessel region corresponding to a blood vessel of the fundus by analyzing the front image and search for the interested region based on a distribution of the blood vessel region in the event that the interested region has not been detected by the first search processor.

The fifth aspect of embodiment examples is the ophthalmologic apparatus of any of the first to third aspects, wherein a size of the template image is smaller than a size of the front image, and the second search processor is configured to create a reduced image of a size corresponding to the size of the template image by resizing the front image, and search for the interested region by applying template matching based on the template image to the reduced image.

The sixth aspect of embodiment examples is the ophthalmologic apparatus of any of the first to third and fifth aspects, wherein the second search processor is configured to pre-store two or more template images respectively corresponding to two or more attributes, and search for the interested region by template matching between each of the two or more template images and the front image.

The seventh aspect of embodiment examples is the ophthalmologic apparatus of any of the first to third, fifth and sixth aspects, wherein the interested region includes an optic nerve head region corresponding to an optic nerve head of the fundus, and the template image is an image of the optic nerve head and vicinity thereof.

The eighth aspect of embodiment examples is the ophthalmologic apparatus of any of the first, second and fourth aspects, wherein the interested region includes an optic nerve head region corresponding to an optic nerve head of the fundus, and the first search processor is configured to search for a boundary of the optic nerve head region by identifying a location in the front image in which a brightness variation is discontinuous.

The ninth aspect of embodiment examples is the ophthalmologic apparatus of any of the second to fourth aspects, wherein the interested region includes an optic nerve head region corresponding to an optic nerve head of the fundus, and the third search processor is configured to search for the optic nerve head region based on one or more parameters among a width, a density and an orientation of the blood vessel region.

The tenth aspect of embodiment examples is the ophthalmologic apparatus of any of the second to fourth and ninth aspects, wherein the front image acquiring device is configured to acquire another front image of the fundus acquired using a modality different from a modality used for acquisition of the front image, and the third search processor is configured to detect a first blood vessel region corresponding to a blood vessel of the fundus by analyzing the another front image, perform registration between the front image and the another front image, identify a second blood vessel region of the front image corresponding to the first blood vessel region based on a result of the registration, and search for the interested region based on a distribution of the second blood vessel region.

The eleventh aspect of embodiment examples is the ophthalmologic apparatus of any of the second to fourth and ninth aspects, wherein the front image acquiring device is configured to acquire another front image of the fundus acquired using a modality different from a modality used for acquisition of the front image, and the third search processor is configured to detect a blood vessel region corresponding to a blood vessel of the fundus by analyzing the another front image, search for a first interested region based on a distribution of the blood vessel region detected from the another front image, perform registration between the front image and the another front image, and identify, as the interested region, a second interested region of the front image corresponding to the first interested region based on a result of the registration.

The twelfth aspect of embodiment examples is the ophthalmologic apparatus of any of the first to eleventh aspects, wherein the front image is obtained by digitally photographing the fundus illuminated with near infrared light.

The thirteenth aspect of embodiment examples is the ophthalmologic apparatus of the twelfth aspect, wherein the front image is a frame of a moving image obtained by repeatedly digitally photographing the fundus illuminated with near infrared light.

The fourteenth aspect of embodiment examples is the ophthalmologic apparatus of the thirteenth aspect, wherein the front image acquiring device includes: an illumination system configured to illuminate the fundus with the near infrared light; and a photographing system that includes an image sensor and configured to repeatedly perform digital photography of the fundus illuminated with the near infrared light, and the ophthalmologic apparatus further includes: a movement mechanism configured to move the illumination system and the photographing system; and a movement processor configured to control the movement mechanism based on a moving image obtained by the photographing system.

The fifteenth aspect of embodiment examples is a method of controlling an ophthalmologic apparatus that includes a processor configured to process a front image of a fundus of a subject's eye, the method comprising: a first search control step that causes the processor to perform a process of searching for an interested region corresponding to an interested site of the fundus based on a brightness variation in the front image; and a second search control step that causes the processor to perform a process of searching for the interested region by template matching between the front image and a template image in the event that the interested region has not been detected by the process performed in the first search control step.

The sixteenth aspect of embodiment examples is the control method of the fifteenth aspect, further comprising a third search control step that causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the second search control step.

The seventeenth aspect of embodiment examples is a method of controlling an ophthalmologic apparatus that includes a processor configured to process a front image of a fundus of a subject's eye, the method comprising: a second search control step that causes the processor to perform a process of searching for an interested region by template matching between the front image and a template image; and a third search control step that causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the second search control step.

The eighteenth aspect of embodiment examples is a method of controlling an ophthalmologic apparatus that includes a processor configured to process a front image of a fundus of a subject's eye, the method comprising: a first search control step that causes the processor to perform a process of searching for an interested region corresponding to an interested site of the fundus based on a brightness variation in the front image; and a third search control step that causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the first search control step.

The nineteenth aspect of embodiment examples is a program configured to cause a computer to execute the method of any of the fifteenth to eighteenth aspects.

The twentieth aspect of embodiment examples is a computer-readable non-transitory recording medium storing the program of the nineteenth aspect.

According to some embodiment examples, the reliability of detection of the interested site of the fundus can be improved.

BRIEF DESCRIPTION OF THE SEVERAL VIEWS OF THE DRAWING

A more complete appreciation of the present invention and many of the attendant advantages thereof will be readily obtained as the same becomes better understood by reference to the following detailed description when considered in connection with the accompanying drawings, wherein:

FIG. 5 is a flowchart illustrating an example of the operation of the ophthalmologic apparatus according to some embodiment examples.

DETAILED DESCRIPTION

Figure 1:
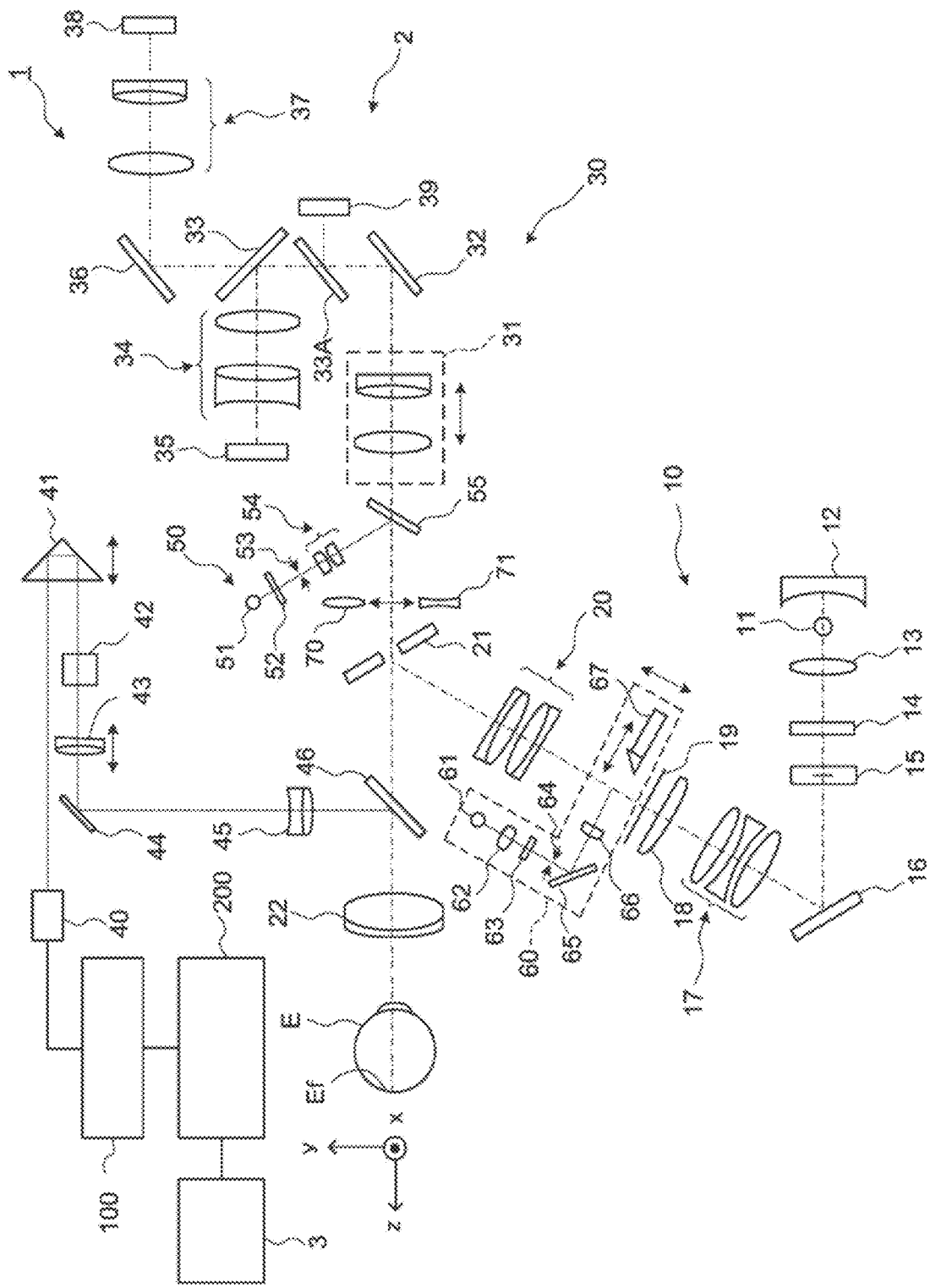
FIG. 1 is a schematic diagram illustrating an example of the configuration of the ophthalmologic apparatus according to some embodiment examples.

An ophthalmologic apparatus, a method of controlling the same, a program and a recording medium according to some embodiment examples will be described in detail with referring to the drawings. Any disclosure contents of the documents cited in the present specification and any existing techniques and technologies may be incorporated in the embodiment examples. Further, "image data" and an "image" created therefrom may not be distinguished unless otherwise mentioned. Similarly, a "site" of the subject's eye and an "image" thereof may not be distinguished unless otherwise mentioned.

The ophthalmologic apparatus according to some embodiment examples may be any apparatus that is capable of acquiring a front image of the fundus of the subject's eye, and may or may not have a function of perform a certain examination on the subject's eye. The function is, for example, an imaging function a photography function, or a measurement function. In the case of having the examination function, the ophthalmologic apparatus has at least a function of processing a front image of eye fundus in addition to the examination function. In the case of not having the examination function, the ophthalmologic apparatus has at least a function of processing a front image of the fundus.

Further, the acquisition of a front image of the fundus performed by the ophthalmologic apparatus according to some embodiment examples may be any of the followings: acquiring a front image by photographing the fundus; and receiving, from an external device, a front image of the fundus acquired in the past by the ophthalmologic apparatus or another ophthalmologic apparatus. Here, examples of the external device include an ophthalmologic apparatus, a computer, a storage device, or a recording medium.

A certain interested site of the fundus of the subject's eye is depicted in the front image of the fundus. In some embodiment examples described below, the interested site is the optic nerve head. However, the interested site is not limited to the optic nerve head, and may be any site of eye fundus such as a macula, a blood vessel, a lesion, or a treatment scar.

The aspects of depiction (or representation) of the interested site may change according to the attributes of subjects and/or subject's eyes. For example, the optic nerve heads of non-white or non-Caucasian persons tend to be depicted relatively bright, while the optic nerve heads of white or Caucasian persons tend to be depicted relatively dark. Therefore, it is conceivable that image processing methods for effectively detecting the interested site from a front image differ depending on the attributes. In some embodiment examples to be described later, the reliability of the interested site detection from a front image is improved by applying two or more image processing methods in a step by step manner.

First Embodiment

The present embodiment provides an exemplary aspect of an ophthalmologic apparatus that has the function of examining the subject's eye. The ophthalmologic apparatus of the present embodiment has the function of measuring the fundi of living eyes using Fourier domain OCT such as swept source OCT, in addition to the function of acquiring front images by photographing the fundi of the living eyes. The types of OCT applicable to some embodiment examples are not limited to swept source OCT, and spectral domain OCT or time domain OCT may be employed, for example. In addition, targeted sites to which OCT is applied are not limited to eye fundus, and OCT may be applied to any sites of eyes such as anterior eye segments or vitreous bodies.

In the present embodiment, a fundus camera is employed as a modality for acquiring a front image of the fundus of the subject's eye. However, the modality for such front image acquisition is not limited to the fundus camera. For example, any modality capable of photographing eye fundi, such as a scanning laser ophthalmoscope (SLO), a slit lamp microscope, or an ophthalmic microscope for surgery, may be employed.

<Configurations>

The ophthalmologic apparatus 1 of the embodiment example shown in FIG. 1 includes the fundus camera unit 2, the OCT unit 100 and the arithmetic and control unit 200. The fundus camera unit 2 is provided with optical systems and mechanisms for acquiring front images of the subject's eye. The OCT unit 100 includes part of optical systems and part of mechanisms for performing OCT. Another part of the optical systems and another part of mechanisms for performing OCT are provided in the fundus camera unit 2. The arithmetic and control unit 200 includes one or more processors that execute various calculations, operations and controls. In addition to these components, the ophthalmologic apparatus 1 may also include arbitrary kinds of elements such as a member for supporting the face of the subject (e.g., a chin rest and/or a forehead rest), and/or arbitrary kinds of units such as a lens unit for switching the sites to which OCT is applied. An example of such a lens unit is an attachment for anterior eye segment OCT.

In the present specification, the term "processor" is used to mean, for example, a circuit such as a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), or the like. The processor realizes the functions according to some embodiment examples, for example, by reading out and executing a program stored in a memory (e.g., a storage circuit or a storage device).

<Fundus Camera Unit 2>

The fundus camera unit 2 is provided with optical systems for photographing the fundus Ef of the subject's eye E. Images of the fundus Ef (referred to as fundus images, fundus photographs, or the like) obtained by the fundus camera unit 2 are front images such as observation images and photographed images. An observation image is obtained, for example, by motion-picture photography using near infrared light. The observation image is used in operations such as alignment, focusing, and tracking. A photographed image is, for example, a still image obtained by using visible or infrared flash light.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2. In addition, the return light of the measurement light from the subject's eye E is directed to the OCT unit 100 through the same optical path.

The light output from the observation light source 11 of the illumination optical system 10 (referred to as observation illumination light) is reflected by the concave mirror 12, passes through the condenser lens 13, and becomes near infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the imaging lens 34. The image sensor 35 detects the return light at a predetermined frame rate (capture rate). Note that the focusing (i.e., the focal position adjustment) of the photographing optical system 30 is performed to focus on the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (i.e., a fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the followings: a fixation position for acquiring an image centered on the macula; a fixation position for acquiring an image centered on the optic nerve head; a fixation position for acquiring an image centered on the position that is located between the macula and the optic nerve head; and a fixation position for acquiring an image of a site far away from the macula (i.e., a periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, which is capable of changing the fixation position, to the subject's eye E is not limited to display devices such as an LCD. For example, a fixation matrix can be adopted in place of a display device. The fixation matrix includes a plurality of light emitting parts (e.g., light emitting diodes) that are disposed in a matrix-like arrangement (in a matrix array). In this case, the fixation position of the subject's eye E by the fixation target can be changed by lighting one (or more) of the plurality of light emitting parts in a selective manner. As another example, the fixation target that is capable of changing the fixation position can be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E (the cornea reflection light, etc.) passes through the same route as that of the return light of the observation illumination light and is guided to the image sensor 35. Based on the received image (referred to as the alignment indicator image), manual alignment and/or automatic alignment can be performed.

As in a conventional case, the alignment indicator image of the present example includes two bright spot images whose positions change according to alignment states. When the relative position between the subject's eye E and the optical system changes in the xy-direction, the two bright spot images are shifted in the xy-direction in an integrated manner. When the relative position between the subject's eye E and the optical system changes in the z-direction, the relative position (i.e., the distance) between the two bright spot images changes. When the distance between the subject's eye E and the optical system in the z-direction matches a predetermined working distance, the two bright spot images overlap with each other. When the position of the subject's eye E matches the position of the optical system in the xy-direction, the two bright spot images are presented within or near a given alignment target. When the distance between the subject's eye E and the optical system in the z-direction matches the working distance, and the position of the subject's eye E matches the position of the optical system in the xy-direction, the two bright spot images overlap with each other and are presented within the alignment target.

In the automatic alignment, the data processor 230 detects the positions of the two bright spot images, and the main controller 211 controls the movement mechanism 150 (described later) on the basis of the positional relationship between the two bright spot images and the alignment target. In the manual alignment, the main controller 211 displays the two bright spot images together with the observation image of the subject's eye E on the display device 241, and the user operates the movement mechanism 150 using the operation device 242 while referring to the two bright spot images displayed.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. Then, the focus light is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (e.g., the fundus reflection light) passes through the same route as the return light of the alignment light and is guided to the image sensor 35. Based on the image (referred to as the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrow in FIG. 1, whereby the length of the measurement arm is changed. The change in the length of the measurement arm can be utilized for correcting the optical path length according to the axial length, and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is moved along the measurement arm in order to perform the focus adjustment of the measurement arm. The movement of the photography focusing lens 31, the movement of the focus optical system 60, and the movement of the OCT focusing lens 43 can be controlled in an interlocking manner.

The optical scanner 44 is placed at a position substantially optically conjugate with the pupil of the subject's eye E. The optical scanner 44 deflects the measurement light LS guided through the measurement arm. An example of the optical scanner 44 is a galvano scanner that allows two dimensional scanning. The galvano scanner includes a galvano mirror for scanning in the x-direction and a galvano mirror for scanning in the y-direction.

<OCT Unit 100>

Figure 2:
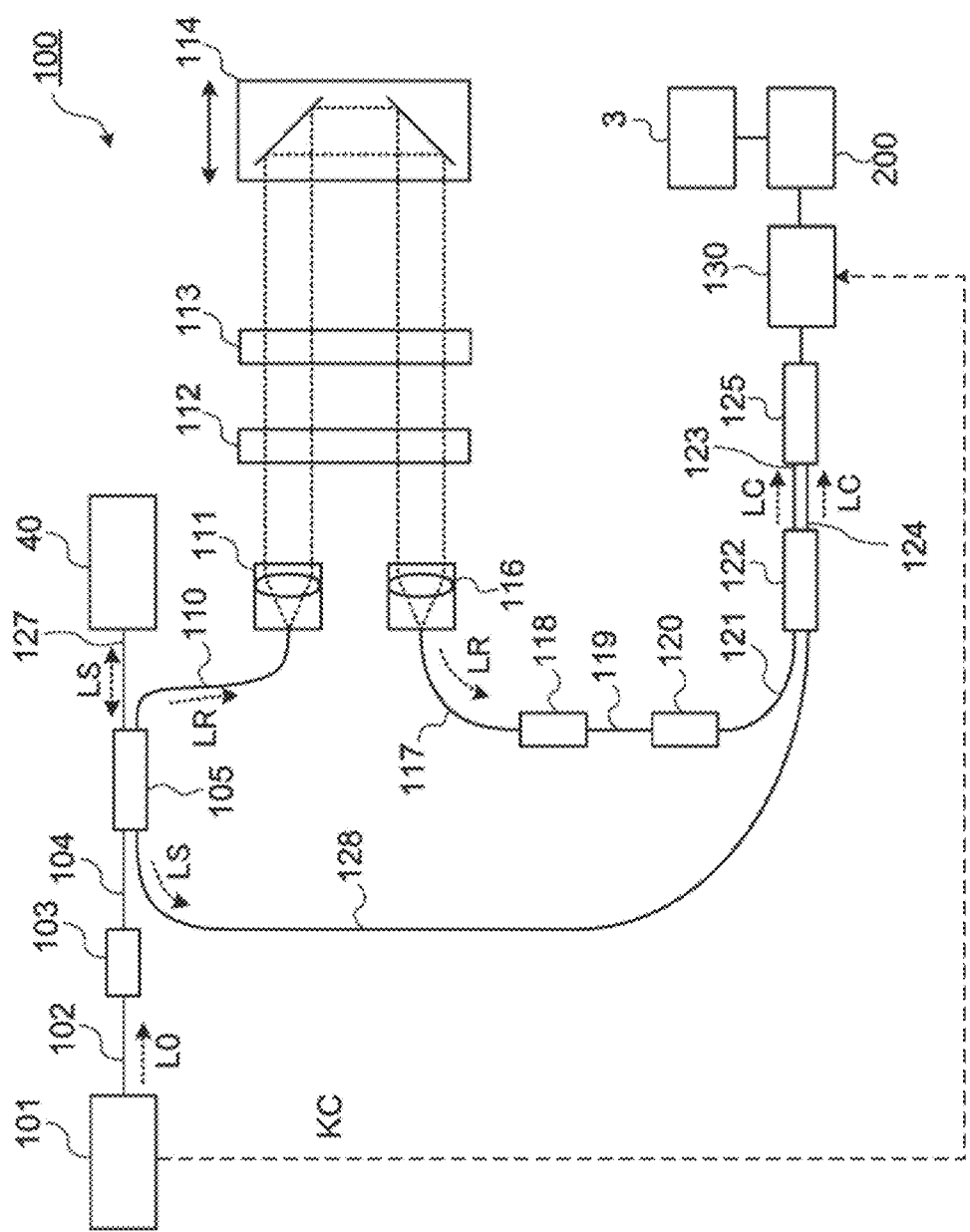
FIG. 2 is a schematic diagram illustrating an example of the configuration of the ophthalmologic apparatus according to some embodiment examples.

As illustrated in FIG. 2, the OCT unit 100 is provided with the optical system for performing swept source OCT. The optical system includes an interference optical system. The interference optical system is configured to split the light emitted from a wavelength tunable light source into measurement light and reference light, superpose the return light of the measurement light returned from the subject's eye E with the reference light having traveled through the reference optical path to generate interference light, and detect the interference light. The result of the detection (i.e., a detection signal) obtained by the interference optical system is a signal representing a spectrum of the interference light. The detection signal is sent to the arithmetic and control unit 200.

The light source unit 101 includes, for example, a near infrared tunable laser configured to vary the wavelengths of emitted light at high speed. The light LO output from the light source unit 101 is guided to the polarization controller 103 through the optical fiber 102, and the polarization state of the light LO is regulated. Further, the light LO is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the length of the reference arm can be utilized, for example, for the correction of the optical path length according to the axial length, and for the regulation of the interference condition.

The reference light LR that has passed through the retroreflector 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The return light of the measurement light LS from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 with the reference light LR incident through the optical fiber 121, to generate interference light. The fiber coupler 122 splits the generated interference light at a predetermined splitting ratio (e.g., the ratio is 1 to 1) to generate a pair of the interference light LC. The pair of the interference light LC is guided to the detector 125 respectively through the optical fibers 123 and 124.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, applies an optical delay to one of the two pieces of split light, superposes the two pieces of split light with each other, detects the superposed light, and generates the clock KC based on the detection result of the superposed light. The data acquisition system 130 uses the clock KC to perform the sampling of the detection signal input from the detector 125. The data acquisition system 130 sends the result of the sampling of the detection signal to the arithmetic and control unit 200.

The present example configuration is provided with both an element for changing the measurement arm length (e.g., the retroreflector 41) and an element for changing the reference arm length (e.g., the retroreflector 114 or a reference mirror); however, only one of these two elements may be provided in some other embodiments. An element for changing the difference between the measurement arm length and the reference arm length (i.e., an element for changing the optical path length difference) is not limited to the aforesaid elements, and may be an element of any type (e.g., an optical member of any type, a mechanism of any type).

<Control System and Processing System>

Figure 3:
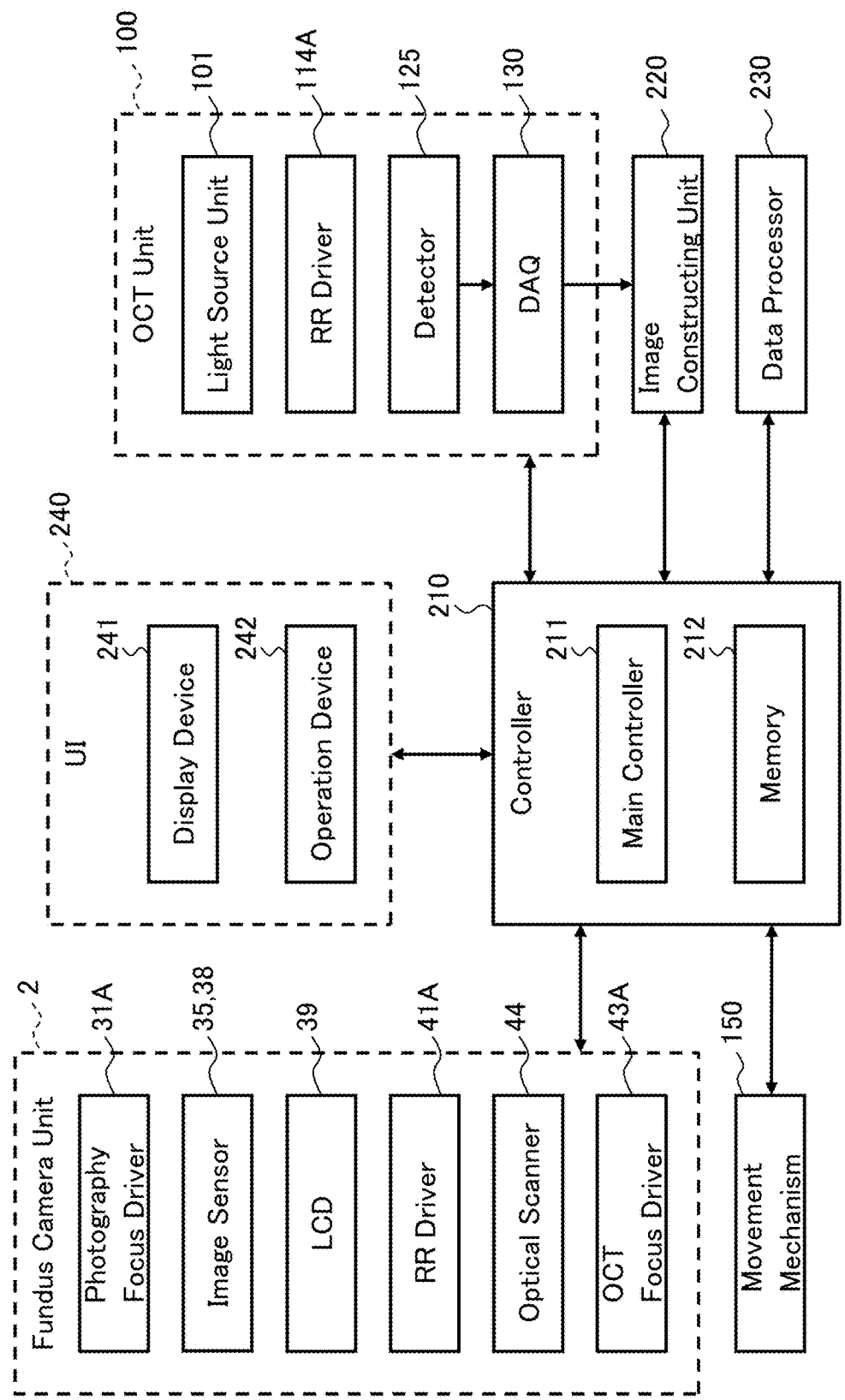
FIG. 3 is a schematic diagram illustrating an example of the configuration of the ophthalmologic apparatus according to some embodiment examples.
Figure 4A:
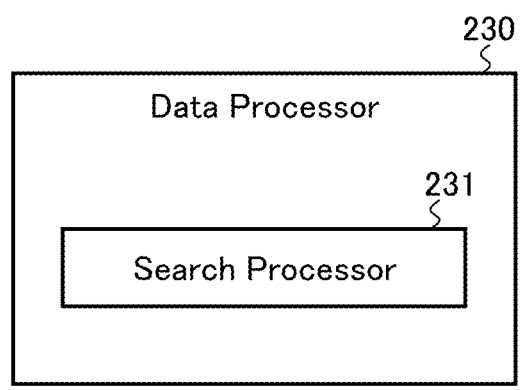
FIG. 4A is a schematic diagram illustrating an example of the configuration of the ophthalmologic apparatus according to some embodiment examples.
Figure 4B:
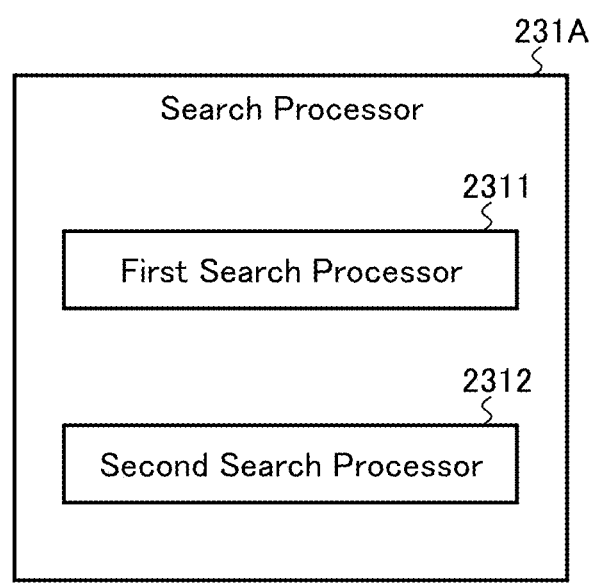
FIG. 4B is a schematic diagram illustrating an example of the configuration of the ophthalmologic apparatus according to some embodiment examples.
Figure 4C:
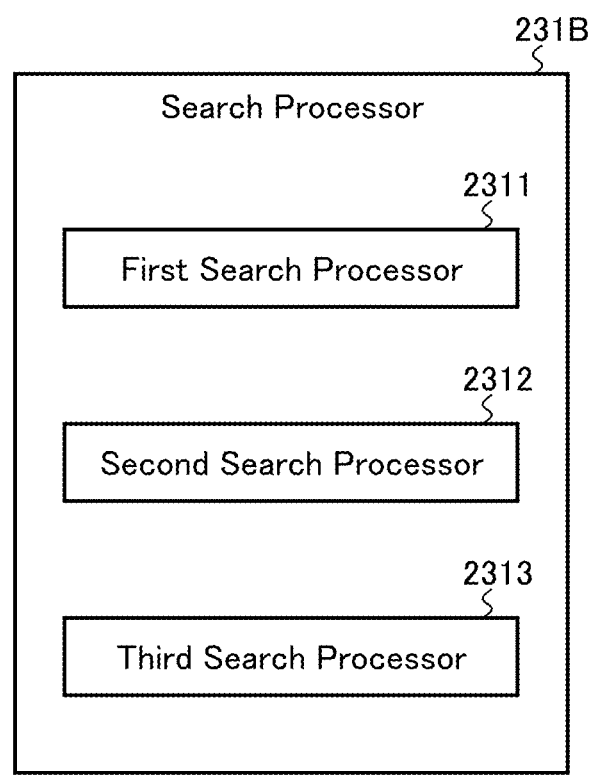
FIG. 4C is a schematic diagram illustrating an example of the configuration of the ophthalmologic apparatus according to some embodiment examples.
Figure 4D:
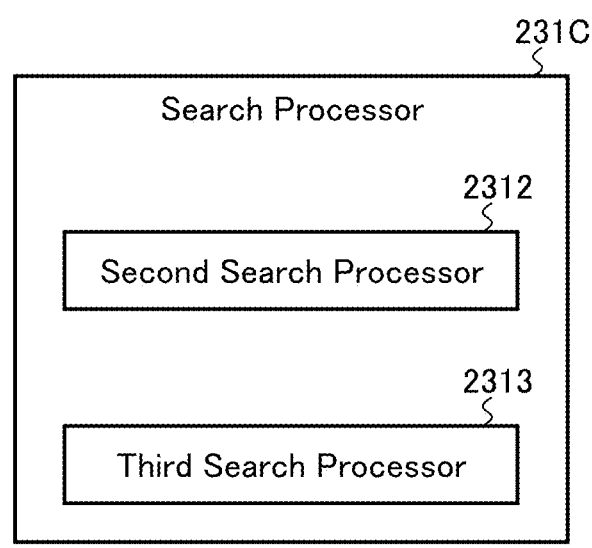
FIG. 4D is a schematic diagram illustrating an example of the configuration of the ophthalmologic apparatus according to some embodiment examples.
Figure 4E:
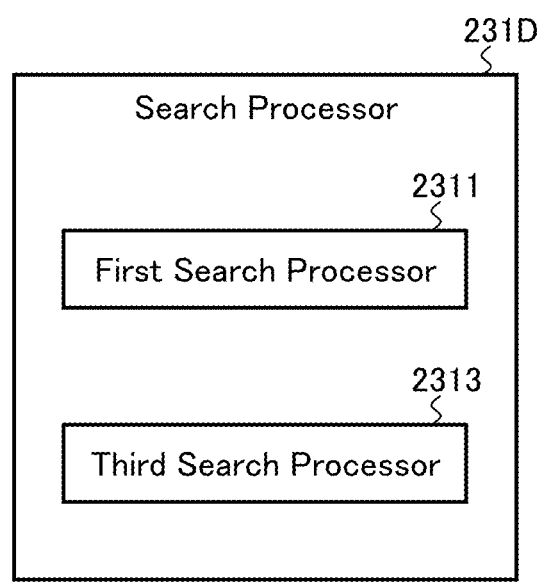
FIG. 4E is a schematic diagram illustrating an example of the configuration of the ophthalmologic apparatus according to some embodiment examples.
Figure 4F:
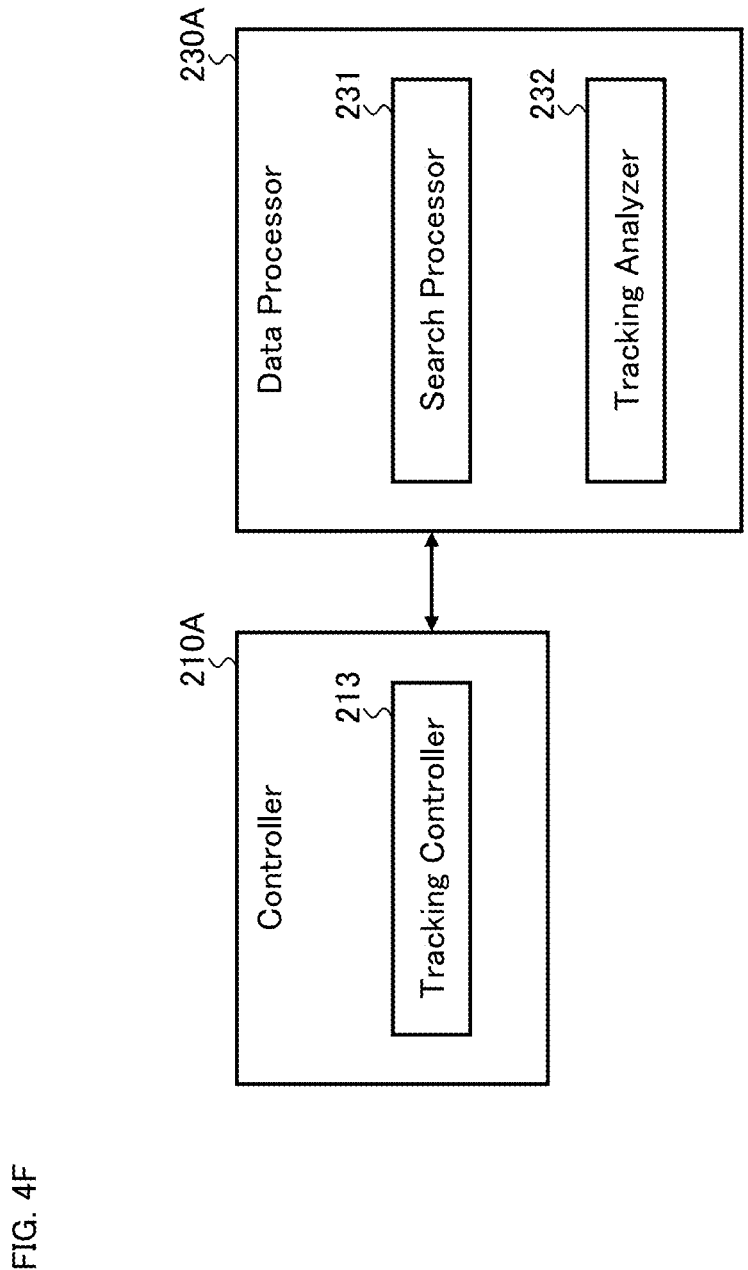
FIG. 4F is a schematic diagram illustrating an example of the configuration of the ophthalmologic apparatus according to some embodiment examples.

FIG. 3 to FIG. 4F show some examples of the configuration of the control system and the processing system of the ophthalmologic apparatus 1. The controller 210, the image constructing unit 220 and the data processor 230 are provided in the arithmetic control unit 200, for example. The ophthalmologic apparatus 1 may include a communication device for performing data communication with an external device. The ophthalmologic apparatus 1 may include a drive device (e.g., a reader and/or a writer) for performing a process of reading data from a recording medium and a process of writing data into a recording medium.

<Controller 210>

The controller 210 performs various kinds of controls. The controller 210 includes the main controller 211 and the memory 212. In addition, as shown in FIG. 4A, the data processor 230 of the present embodiment includes the search processor 231. FIG. 4B to FIG. 4E show some examples of the configuration of the search processor 231. FIG. 4F shows an example of the configuration of the combination of the controller 210 and the data processor 230. These configuration examples may be selectively employed. Note that configurations employable in embodiments are not limited to these configuration examples.

<Main Controller 211>

The main controller 211 includes one or more processors and controls each element of the ophthalmologic apparatus 1 (including the elements shown in FIG. 1 to FIG. 4F). The main controller 211 is realized by the cooperation of hardware including the processors and control software.

Under the control of the main controller 211, the photography focus driver 31A moves the photography focusing lens 31 disposed in the photographing optical path and the focus optical system 60 disposed in the illumination optical path. Under the control of the main controller 211, the retroreflector driver (RR driver, for short) 41A moves the retroreflector 41 disposed in the measurement arm. Under the control of the main controller 211, the OCT focus driver 43A moves the OCT focusing lens 43 disposed in the measurement arm. The optical scanner 44 disposed in the measurement arm operates under the control of the main controller 211. The retroreflector driver (RR driver, for short) 114A moves the retroreflector 114 disposed in the reference arm under the control of the main controller 211. Each of the aforesaid drivers includes an actuator, such as a pulse motor, that operates under the control of the main controller 211.

The movement mechanism 150 moves, for example, at least the fundus camera unit 2 in a three dimensional manner. In a typical example, the movement mechanism 150 includes the followings: an x-stage movable in the ±x-direction (i.e., left and right direction); an x-movement mechanism that moves the x-stage; a y-stage movable in the ±y-direction (i.e., up and down direction); a y-movement mechanism that moves the y-stage; a z-stage movable in the ±z-direction (i.e., depth direction); and a z-movement mechanism that moves the z-stage. Each of the aforesaid movement mechanisms includes an actuator, such as a pulse motor, that operates under the control of the main controller 211.

<Memory 212>

The memory 212 stores various kinds of data. Examples of the data stored in the memory 212 include OCT images, fundus images, and subject's eye information. The subject's eye information includes: subject information such as the patient ID, the patient's name, and the patient's attributes; identification information for the left eye and the right eye; and electronic medical record information.

<Image Constructing Unit 220>

The image constructing unit 220 includes one or more processors, and constructs OCT image data of the fundus Ef based on signals (sampling data) input from the data acquisition system 130. The OCT image data is, for example, B-scan image data, that is, two dimensional cross sectional image data. The B-scan image data is image data constructed by arranging a plurality of pieces of A-scan data obtained respectively for a plurality of scan points arranged along a straight line (i.e., for a scan point sequence), according to the positional relationship of the scan points.

The processing for constructing OCT image data includes noise elimination (or noise reduction), filtering, fast Fourier transform (FFT), and other processes as in a conventional Fourier domain OCT. In the event where another type of OCT apparatus is employed, the image constructing unit 220 performs known processing according to the OCT type employed.

The image constructing unit 220 constructs three dimensional data of the fundus Ef based on signals input from the data acquisition system 130. The three dimensional data is three dimensional image data representing a three dimensional region (i.e., a volume) of the fundus Ef. Three dimensional image data means image data in which pixel positions are defined using a certain three dimensional coordinate system. Stack data and volume data are examples of three dimensional image data.

Stack data is image data constructed by three dimensionally arranging a plurality of cross sectional images respectively obtained along a plurality of scan lines, based on the positional relationship of the scan lines. In other words, stack data is image data constructed by representing a plurality of cross sectional images, which are originally defined using individually different two dimensional coordinate systems, using a common single three dimensional coordinate system. In other words, stack data is constructed by embedding such cross sectional images in a single three dimensional space. Alternatively, stack data is image data constructed by three dimensionally arranging a plurality of pieces of A-scan data obtained respectively for a plurality of scan points arranged in a two dimensional manner (i.e., obtained for scan point array), based on the positional relationship of the scan points.

Volume data is image data whose picture elements are voxels that are arranged in a three dimensional manner. Volume data is also referred to as voxel data. Volume data is constructed by applying known interpolation, voxelization, etc. to stack data.

The image constructing unit 220 constructs an image to be displayed, by applying rendering to three dimensional image data. Examples of rendering techniques applicable to this image construction include volume rendering, surface rendering, maximum intensity projection (MIP), minimum intensity projection (MinIP), and multi planar reconstruction (MPR).

The image constructing unit 220 may be configured to construct an OCT front image (also referred to as an OCT en-face image) based on three dimensional image data. For example, the image constructing unit 220 may be configured to construct projection data by projecting three dimensional image data in the z-direction (i.e., the A-line direction, the depth direction). Further, the image constructing unit 220 may be configured to construct a shadowgram by projecting partial data of three dimensional image data in the z-direction.

Partial three dimensional image data (slab) used for the shadowgram construction is set, for example, using segmentation. Segmentation is processing of identifying a partial region in an image. Typically, segmentation is used to identify an image region corresponding to a predetermined tissue of the fundus Ef. Segmentation is performed, for example, by the image constructing unit 220 or the data processor 230.

The ophthalmologic apparatus 1 may be capable of performing OCT angiography. OCT angiography is an imaging technique that constructs an image in which retinal blood vessels and choroidal blood vessels are emphasized. This technique is disclosed, for example, in Japanese Unexamined Patent Application Publication No. 2015-515894 that is the translation of international publication No. WO2013/167641. Generally, the blood flows inside blood vessels vary within a short period of time while fundus tissues (i.e., fundus structures) do not. OCT angiography generates an image by emphasizing the locations (e.g., blood flow signals) in which such time-dependent changes exist. OCT angiography is also referred to as OCT motion contrast imaging or the like. In addition, images obtained by OCT angiography are referred to as (OCT) angiographic images, (OCT) angiograms, motion contrast images, or the like.

When performing OCT angiography, the ophthalmologic apparatus 1 repeatedly scans the same region of the fundus Ef a predetermined number of times. For example, the ophthalmologic apparatus 1 may perform repetitive scanning along a path between two points on a predetermined scan pattern (e.g., a spiral scan pattern). The image constructing unit 220 may construct a motion contrast image from the data set acquired by the data acquisition system 130 through the repetitive scanning. The motion contrast image is an angiographic image constructed by imaging and emphasizing a temporal change in the interference signals caused by blood flows in the fundus Ef. Typically, OCT angiography is applied to a three dimensional region of the fundus Ef, to acquire an image representing a three dimensional distribution of blood vessels of the fundus Ef.

When OCT angiography has been performed, the image constructing unit 220 may construct any kind of two dimensional angiographic image data and/or any kind of pseudo three dimensional angiographic image data, from three dimensional angiographic image data. For example, the image constructing unit 220 may construct two dimensional angiographic image data representing a desired cross section of the fundus Ef, by applying multi planar reconstruction to three dimensional angiographic image data.

The image constructing unit 220 is realized by the cooperation of hardware including the processors and image construction software.

<Data Processor 230>

The data processor 230 includes one or more processors, and applies various kinds of data processing to an image of the subject's eye E. For example, the data processor 230 is realized by the cooperation of hardware including the processors and data processing software.

The data processor 230 may perform position matching (i.e., registration) between two images acquired for the fundus Ef. For example, the data processor 230 may perform registration between three dimensional image data acquired by OCT and a front image acquired by the fundus camera unit 2. Further, the data processor 230 may perform registration between two OCT images acquired by OCT. Furthermore, the data processor 230 may perform registration between two front images acquired by the fundus camera unit 2. In addition, registration may be applied to an analysis result of an OCT image and/or an analysis result of a front image. Such registration may be performed by any known method or technique, and includes, for example, feature point extraction and affine transformation.

<Search Processor 231>

As shown in FIG. 4A, the data processor 230 of the present embodiment includes the search processor 231. The search processor 231 performs processing of searching for an interested region (i.e., a region of interest or a ROI) corresponding to a predetermined interested site from a front image of the fundus Ef. The search processor 231 is realized by the cooperation of hardware including one or more processors and search software.

A front image processed by the search processor 231 is, for example, an image acquired by photographing the fundus Ef with the fundus camera unit 2, and is typically an observation image of the fundus Ef (one or more frames of the observation image). In other words, a front image processed by the search processor 231 may be, for example, an image obtained by digitally photographing the fundus Ef illuminated with the observation illumination light from the illumination optical system 10, wherein the digital photography is performed using the image sensor 35 of the photographing optical system 30, and may be typically one or more frames of an observation image obtained by repeatedly performing digital photography on the fundus Ef illuminated with the observation illumination light using the image sensor 35. Note that, a front image processed by the search processor 231 is not limited to the above examples, and may be an image acquired by photographing the fundus Ef with another ophthalmologic apparatus, for example.

As described above, the search processor 231 of the present embodiment may be any one of the example shown in FIG. 4B (the search processor 231A), the example shown in FIG. 4C (the search processor 231B), the example shown in FIG. 4D (the search processor 231C), and the example shown in FIG. 4E (the search processor 231D). Alternatively, although not illustrated in the drawings, the search processor 231 of the present embodiment may have a configuration different from these examples. The examples shown in FIG. 4B to FIG. 4E will be described below. A typical example of the interested site searched for in these examples is assumed to be an optic nerve head (optic disc, optic papilla). An interested region corresponding to an optic nerve head is referred to as an optic nerve head region.

<Search Processor 231A>

The search processor 231A shown in FIG. 4B includes the first search processor 2311 and the second search processor 2312. The first search processor 2311 is realized by the cooperation of hardware including one or more processors and first search software. The second search processor 2312 is realized by the cooperation of hardware including one or more processors and second search software.

For example, the search processor 231A is configured to complete the search process in the event that the search for an interested region by the first search processor 2311 has been successful. Further, the search processor 231A is configured to shift to the search for the interested region by the second search processor 2312 in the event that the search for the interested region by the first search processor 2311 has failed. Here, at least part of the search process performed by the first search processor 2311 is different from at least part of the search process performed by the second search processor 2312. In this way, the search processor 231A may improve the reliability of the interested site detection by applying two mutually different search processes to the front image in a step by step manner.

<First Search Processor 2311>

The first search processor 2311 is configured to search for an interested region based on brightness variation in a front image of the fundus Ef.

When searching for an optic nerve head region corresponding to the optic nerve head of the fundus Ef, the first search processor 2311 is configured to search for an image region corresponding to the edge (fringe, rim, periphery) of the optic nerve head based on the brightness variation in the front image, for example. To that end, the first search processor 2311 may be configured to apply a known edge detection algorithm to the front image to identify a location in the front image at which the brightness variation is discontinuous, for example. That is, the first search processor 2311 may be configured to identify a location at which the image brightness varies sharply, for example. Thereby, the first search processor 2311 may search for the boundary of the optic nerve head region in the front image.

The edge detection algorithm may employ a search-based algorithm or a zero-crossing based algorithm. The search-based algorithm typically includes the following steps: a step of obtaining a measure of edge strength by calculating the gradient with a first-order derivative expression; a step of estimating the local orientation of the edge from the direction of the gradient; and a step of searching for a location at which the gradient in the estimated direction becomes a local maxima. The zero-crossing based algorithm includes, for example, a step of searching for a zero-crossing in a second-order derivative expression, and typically includes a step of searching for a zero-crossing in the Laplacian or a step of searching for a zero-crossing in a non-linear differential expression. Note that the first search processor 2311 may apply smoothing (typically, Gaussian smoothing) to the front image as pre-processing for the edge detection. The edge detection algorithm applicable to the present example may be based on any known method or technique such as the Canny edge detector, the Canny-Deriche detector, the Marr-Hildreth algorithm, or the differential edge detection.

Such edge detection algorithms are particularly effective for detecting a target site that is depicted relatively brightly and whose contour (edge) is represented relatively clearly, like the optic nerve head of the persons who are Mongoloid in race. On the other hand, the above edge detection algorithms are less effective in the case where the image of a target site is represented relatively darkly and whose contour (edge) is represented relatively unclearly, such as the image of the optic nerve head of the persons who are Caucasian in race.

The calculation resources required for the edge detection executed by the first search processor 2311 are generally smaller than the calculation resources required for template matching executed by the second search processor 2312 described later. Therefore, the efficiency of the entire processing improves with the configuration of arranging edge detection and template matching in this order and of performing the template matching if the edge detection has failed.

<Second Search Processor 2312>

The second search processor 2312 is configured to search for an interested region by template matching between a front image of the fundus Ef and a template image. The template matching in the present example is performed in the event that the interested region has not been detected by the first search processor 2311.

Some examples of processing employable in the template matching performed by the second search processor 2312 are described below. Any one or more of these processing examples may be incorporated into the template matching.

The template image is an image representing a region of eye fundus that includes at least the interested region. The template image may be an image acquired by photographing a fundus of a standard eye. The standard eye may be, for example, an eye in which the presence of a lesion is not recognized (normal eye, healthy eye), or an eye in which a specific lesion is observed (affected eye). In addition, the template image may be a single photographed image or an image obtained by cropping a single photographed image. Alternatively, the template image may be an image created from two or more photographed images obtained by photographing a single eye multiple times, or an image created from two or more photographed images obtained by photographing two or more eyes. For example, the template image may be created by applying image composition, such as averaging, to two or more photographed images. Furthermore, the template image may be created from a processed image obtained by processing one or more photographed images. The template image created in such a way is stored in the second search processor 2312. The created template image may also be stored in the memory 212.

The size of the template image may be arbitrary. Here, the image size is typically defined by the number of pixels. In the present example, both the front image and the template image are two dimensional images in which pixel positions are defined in the xy-coordinate system or in a corresponding two dimensional image space. The image size of a two dimensional image is typically defined by the number of pixels in the first coordinate axis direction and the number of pixels in the second coordinate axis direction orthogonal to the first coordinate axis direction.

In some embodiment examples, the size of the template image may be smaller than the size of the front image of the fundus Ef used for template matching. Typically, the number of pixels of the front image in the first coordinate axis direction may be an integral multiple (M times) of the number of pixels of the template image in the first coordinate axis direction, and the number of pixels of the front image in the second coordinate axis direction may be an integral multiple (N times) of the number of pixels of the template image in the second coordinate axis direction. Here, one of M and N is an integer equal to or greater than 1, and the other is an integer equal to or greater than 2. Typically, both M and N are integers equal to or greater than 2, and M=N. With such a setting, the image size ratio in the first coordinate axis direction and the image size ratio in the second coordinate axis direction become equal to one another, and this facilitates the comparison of interested site images.

If the size of the template image is smaller than the size of the front image, the second search processor 2312 may first apply a known resizing algorithm to the front image to create a reduced image of the size corresponding to the size of the template image. For example, the second search processor 2312 may create a reduced image of one-sixteenth (¹⁄₁₆) the size of the front image.

Next, the second search processor 2312 may search for an image in the reduced image corresponding to the interested site, by applying template matching based on the template image to the reduced image. The image corresponding to the interested site is the interested region.

If the interested region has been detected from the reduced image, the second search processor 2312 may identify the image region in the front image corresponding to the interested region in the reduced image, and treat the identified image region as the interested region in the front image. Here, the interested region in the front image may be determined by performing specific processing on the image region in the front image corresponding to the interested region in the reduced image. For example, image processing for restoring information lost due to resizing for creating a reduced image from a front image may be applied. Typically, the second search processor 2312 may apply edge detection etc. to the contour of the image region in the front image corresponding to the interested region in the reduced image and its vicinity, to detect small irregularities of the contour that have been lost by resizing.

While the resizing may be enlargement, reduction employed in the present example has at least the following advantages. Namely, the first advantage is that the influence of individual differences in the size of the interested site may be lessened. The second advantage is that the computational resources required for template matching may be reduced.

Another example of processing employable in template matching will be described. As described above, the aspect of representation of an interested region tends to vary according to attributes of subjects and/or subject's eyes. Considering this fact, two or more template images respectively corresponding to two or more attributes may be prepared. For example, a template image corresponding to the optic nerve heads of the persons who are Mongoloid in race, and a template image corresponding to the optic nerve heads of the persons who are Caucasian in race may be prepared.

The second search processor 2312 may store in advance two or more template images respectively corresponding to two or more attributes. Further, the second search processor 2312 may search for an interested region in the front image by template matching between each of the template images and the front image.

For example, when the first template image corresponding to the optic nerve heads of the persons who are Mongoloid in race and the second template image corresponding to the optic nerve heads of the persons who are Caucasian in race are prepared, the second search processor 2312 may perform both the search for an interested region in the front image by template matching between the first template image and the front image, and the search for an interested region in the front image by template matching between the second template image and the front image.

The timing for performing two or more template matching processes based respectively on two or more template images is arbitrary. For example, two or more template matching processes may be performed as serial processing, or some of two or more template matching processes may be performed as parallel processing.

The order of executing two or more template matching processes may be arbitrary. For example, the user may set the execution order, or the ophthalmologic apparatus 1 (e.g., the controller 210, the data processor 230, or other elements) may be configured to set the execution order. In the latter case (i.e., in the case of automatic setting), for example, the ophthalmologic apparatus 1 may be configured to acquire the attributes of the subject and/or the subject's eye from the subject information stored in the memory 212 and then set the execution order based on the acquired attributes. Alternatively, the ophthalmologic apparatus 1 may be configured to set the execution order based on the country and/or the region in which the ophthalmologic apparatus 1 is installed.

In some embodiment examples, the second search processor 2312 may be configured to perform all of the two or more template matching processes respectively corresponding to the prepared two or more template images. In this case, for example, the second search processor 2312 obtains a final detection result of the template matching based on two or more results obtained by the two or more template matching processes. Here, the two or more results obtained by the two or more template matching processes include, for example, an interested region obtained from successful detection and/or the fact that detection has failed in the event of detection failure. Typically, the final detection result is obtained in any of the following ways: (1) In the event where the detections have failed in all template matching processes, the final detection result also becomes detection failure; (2) In the event where a detection has been successful in only one of the two or more template matching processes, the interested region detected by the successful detection becomes the final detection result; (3) In the event where detections have been successful in any two or more of the two or more template matching processes, any one of two or more interested regions detected by the two or more successful template matching processes is selected, and the selected interested region becomes the final detection result (here, for example, an interested region with the highest matching degree (e.g., image correlation, etc.) is selected; and (4) In the event where detections have been successful in any two or more of the two or more template matching processes, the final detection result is obtained by composing (e.g., averaging, etc.) two or more of two or more interested regions detected by the two or more successful template matching processes.

In contrast, in some other embodiment examples, the second search processor 2312 may be configured to be capable of performing only part of two or more template matching processes respectively corresponding to two or more prepared template images. Note that, in some cases, the second search processor 2312 may be configured to perform all of the two or more template matching processes. For example, when applying some of the two or more template images as serial processing, the second search processor 2312 may be configured to quit the processing at the stage where a template matching process has achieved a matching degree (image correlation, etc.) that is equal to or greater than a predetermined threshold value. Note that if a suitable interested region has been detected in the last template matching in the series, or if no suitable interested region has been detected in all template matching processes, all of the two or more template matching processes are performed. This concludes the description of the example shown in FIG. 4B (the search processor 231A).

Next, the example shown in FIG. 4C (the search processor 231B) will be described. The search processor 231B includes the first search processor 2311, the second search processor 2312, and the third search processor 2313. The first search processor 2311 and the second search processor 2312 may be configured in the same manner as those in the search processor 231A, and thus, the description thereof will be omitted to avoid redundancy. The third search processor 2313 is realized by the cooperation of hardware including one or more processors and third search software.

For example, if the search for an interested region by the first search processor 2311 has been successful, the search processor 231B may finish the serial search processing at this stage. On the other hand, if the search for an interested region by the first search processor 2311 has failed, the search processor 231B may start the search for an interested region by the second search processor 2312. It should be noted that at least part of the search process performed by the first search processor 2311 is different from at least part of the search process performed by the second search processor 2312.

Similarly, if the search for an interested region by the second search processor 2312 has been successful, the search processor 231B may finish the serial search processing at this stage. On the other hand, if the search for an interested region by the second search processor 2312 has failed, the search processor 231B may start the search for an interested region by the third search processor 2313. Here, at least part of the search process performed by the third search processor 2313 is different from both at least part of the search process performed by the first search processor 2311 and at least part of the search process performed by the second search processor 2312.

As described above, the search processor 231B serves to improve the reliability of the interested site detection by applying three mutually different search processes to a front image in a step by step manner.

<Third Search Processor 2313>

The third search processor 2313 is configured to perform blood vessel detection and interested region search. The blood vessel detection is a process of detecting a blood vessel region corresponding to a blood vessel of the fundus Ef by analyzing a front image of the fundus Ef. The interested region search is a process of searching for an interested region corresponding to the interested site of the fundus Ef based on the distribution of the blood vessel region obtained by the blood vessel detection.

Described below are some examples of the blood vessel detection executable by the third search processor 2313. The blood vessel detection is performed according to a blood vessel detection program included in the third search software. For example, the third search processor 2313 may be configured to detect a blood vessel region by applying thresholding related to brightness and/or shape analysis of an image region (pattern matching, etc.) to a front image of the fundus Ef. Typically, the third search processor 2313 may be configured to detect a blood vessel region by searching for an image region of linear shape and with brightness higher (or lower) than its surroundings (neighborhood, vicinity). In addition to the above examples, the blood vessel detection may include image processing such as labeling, region growing, edge detection, thresholding, or the like.

The third search processor 2313 performs the interested region search based on the distribution of the blood vessel region detected by such blood vessel detection. Some examples of the interested region search that the third search processor 2313 may perform are described below.

If the interested site is the optic nerve head (i.e., if the interested region includes the optic nerve head region), the third search processor 2313 may perform a search for the optic nerve head region based on one or more parameters relating to blood vessels. For example, the third search processor 2313 may be configured to search for the optic nerve head region based on one or more parameters of the blood vessel region chosen from among the width (blood vessel width, blood vessel diameter), the density (blood vessel density) and the orientation (blood vessel orientation).

The process of calculating the blood vessel diameter includes, for example, a process of determining the traveling direction (running direction, tracking direction) of the blood vessel at a certain location in the blood vessel region, and a process of calculating the diameter of the blood vessel at this location based on the blood vessel traveling direction determined. The process of determining the blood vessel traveling direction at a certain location in the blood vessel region may include a process of creating a wire model of the blood vessel region by applying thinning to the blood vessel region, and a process of determining the slope (gradient, blood vessel orientation) of the wire model at the concerned location. The process of calculating the blood vessel diameter at the concerned location based on the blood vessel traveling direction may include a process of calculating the size of the blood vessel region in the direction orthogonal to the slope (gradient) of the wire model at the concerned location.

The process of obtaining the blood vessel density includes, for example, a process of calculating the ratio of the blood vessel region to an image region (a partial region of the front image) having a predetermined size (and a predetermined shape). The ratio is calculated, for example, by dividing the area (number of pixels) of the blood vessel region by the area (number of pixels) of the concerned image region.

The optic nerve head is the exit for optic nerves and also the gateway for main blood vessels that supplies blood to eye fundus tissues. Many thick blood vessels exist near the optic nerve head in comparison with other regions. Generally, blood vessels near the optic nerve head run radially about the optic nerve head. In this way, blood vessels near the optic nerve head have a characteristic distribution. More specifically, from a standard and general viewpoint, eye fundus blood vessels have the following characteristics, features and tendencies: (1) The diameters of blood vessels near the optic nerve head are greater than those of blood vessels in other regions (for example, the average blood vessel diameter near the optic nerve head is greater than those in other regions); (2) The blood vessel density near the optic nerve head is higher than those in other regions; (3) The blood vessel orientation near the optic nerve head is along a radial direction with respect to the optic nerve head or a direction close to the radial direction.

Such characteristics of the blood vessel distribution may be used to search for the optic nerve head region. For example, the optic nerve head region may be searched for by doing any of the followings: calculating the blood vessel diameters; creating a histogram of the blood vessel diameters; comparing the blood vessel diameters; calculating a statistic of the blood vessel diameters (e.g., mean, median, mode, variance, standard deviation, etc.); calculating the number or percentage of blood vessels with diameters equal to or greater than a predetermined threshold; calculating the blood vessel densities; creating a histogram of the blood vessel densities; comparing the blood vessel densities; calculating a statistic of the blood vessel densities; determining the blood vessel orientations; calculating a statistic of the blood vessel orientations; and comparing the blood vessel orientations.

Another example of the interested region search executable by the third search processor 2313 will be described. In the present example, the ophthalmologic apparatus 1 is configured to be capable of acquiring two or more types of front images respectively acquired by using two or more types of modalities. Among these front images, the first type of a front image is referred to as the first front image, and the second type of a front image is referred to as the second front image.

When the first front image and the second front image are acquired for the fundus Ef, the third search processor 2313 may be configured to be able to perform the following series of processes.

First, the third search processor 2313 detects the first blood vessel region corresponding to a blood vessel of the fundus Ef by analyzing the first front image. This process may be performed in the same manner as the blood vessel detection described above. Next, the third search processor 2313 performs registration between the first front image and the second front image. Subsequently, the third search processor 2313 identifies the second blood vessel region in the second front image corresponding to the first blood vessel region in the first front image, based on the registration result, in other words, based on the correspondence of positions (pixels) between the first front image and the second front image. Further, the third search processor 2313 searches for an interested region based on the distribution of the second blood vessel region identified.

Typically, the first front image is of higher quality than the second front image. Here, the quality of a front image corresponds at least to the clarity of the depiction of blood vessels. That is, blood vessels are clearly depicted in a high-quality front image, and blood vessels are unclearly depicted in a low-quality front image. In a typical example, the first front image may be any of an OCT angiogram, a photographed image (e.g., a color fundus image), and a fluorescent contrast image (e.g., a fluorescein fluorescent contrast image, indocyanine green fluorescent contrast image) while the second front image is a frame of an observation image.

According to the processing of the present example, an interested region in the second front image with a relatively low image quality may be detected by combining blood vessel detection to the first front image with a relatively high image quality and registration. For example, a blood vessel region may be effectively detected from an observation image with a relatively low image quality, wherein the observation image have been obtained by near infrared imaging.

Another processing example applicable in the event that the first front image and the second front image are acquired for the fundus Ef will be described. In the present example, the third search processor 2313 is configured to be able to perform the following series of processes.

First, the third search processor 2313 detects the first blood vessel region corresponding to the blood vessel of the fundus Ef by analyzing the first front image. Next, the third search processor 2313 searches for the first interested region based on the distribution of the first blood vessel region. Subsequently, the third search processor 2313 performs registration between the first front image and the second front image. Further, the third search processor 2313 identifies, as an interested region, the second interested region in the second front image corresponding to the first interested region. Here, the identification of the second interested region is performed based on the registration result, in other words, based on the correspondence of positions (pixels) between the first front image and the second front image.

According to the processing of the present example as well, an interested region in the second front image with a relatively low image quality may be detected by combining blood vessel detection to the first front image with a relatively high image quality and registration. For example, a blood vessel region may be effectively detected from an observation image with a relatively low image quality that have been obtained by near infrared imaging.

The retinal pigment epithelium may become thinner due to aging or high myopia, and then choroidal blood vessels may appear in a fundus front image. Such an eye fundus is referred to as a tigroid fundus, a tessellated fundus, or the like. While both retinal blood vessels and choroidal blood vessels are depicted in a front image of a tigroid fundus, the retinal blood vessels are the targets for the blood vessel detection executed by the third search processor 2313. The third search processor 2313 may be configured to selectively detect retinal blood vessels from a front image of a tigroid fundus. For example, the third search processor 2313 may be configured to detect regions with tigroid patterns from a front image of a tigroid fundus and then detect retinal blood vessels from other regions. Alternatively, the third search processor 2313 may be configured to selectively detect retinal blood vessels from a front image of a tigroid fundus, based on the difference between the depiction aspects of choroidal blood vessels and those of retinal blood vessels. The depiction aspects may be the shapes, brightness, clarity of the contours, for example.

The calculation resources required for the template matching executed by the second search processor 2312 are generally smaller than those required for the combination of the blood vessel detection and the interested region search executed by the third search processor 2313. Therefore, the efficiency of these two processes as a whole may be enhanced by arranging the template matching and the combination of the blood vessel detection and the interested region search in this order and by performing the combination of the blood vessel detection and the interested region search only if the template matching has failed.

In addition, as described above, the calculation resources required for the edge detection executed by the first search processor 2311 are generally smaller than those required for the template matching executed by the second search processor 2312. In this viewpoint, the efficiency of these two processes as a whole may be enhanced by arranging the edge detection and the template matching in this order and by performing the template matching only if the edge detection has failed.

The search processor 231B in the present example may perform processing in which processes are combined in this way. More specifically, the search processor 231B may be configured in the following manner: to end the search processing if the search for an interested region by the first search processor 2311 has been successful; to start the search for an interested region by the second search processor 2312 if the search for an interested region by the first search processor 2311 has failed; to end the search processing if the search for an interested region by the second search processor 2312 has been successful; and to start the search for an interested region by the third search processor 2313 if the search for an interested region by the second search processor 2312 has failed. By having such a configuration, the efficiency of the three search processes as a whole may be improved.

Next, the example shown in FIG. 4D (the search processor 231C) will be described. The search processor 231C includes the second search processor 2312 and the third search processor 2313. The second search processor 2312 and the third search processor 2313 may be configured in the same manner as those described above, and the description thereof will be omitted.

For example, the search processor 231C is configured to end the search processing if the search for an interested region by the second search processor 2312 has been successful, and start the search for an interested region by the third search processor 2313 if the search for an interested region by the second search processor 2312 has failed.

According to the search processor 231C having such a configuration, the reliability of the interested site detection processing may be improved by applying two mutually different search processes to a front image in a step by step manner. In addition, the search processor 231C having such a configuration may promote the efficiency of the two processes as a whole.

Next, the example shown in FIG. 4E (the search processor 231D) will be described. The search processor 231D includes the first search processor 2311 and the third search processor 2313. The first search processor 2311 and the third search processor 2313 may be configured in the same manner as those described above, and the description thereof will be omitted.

For example, the search processor 231D is configured to end the search processing if the search for an interested region by the first search processor 2311 has been successful, and start the search for an interested region by the third search processor 2313 if the search for an interested region by the first search processor 2311 has failed.

According to the search processor 231D having such a configuration, the reliability of the interested site detection processing may be improved by applying two mutually different search processes to a front image in a step by step manner. In addition, the search processor 231D having such a configuration may promote the efficiency of the two processes as a whole.

Next, the example shown in FIG. 4F will be described. The ophthalmologic apparatus 1 of the present example is configured to be capable of performing tracking for adjusting the positions of the illumination optical system 10 and the photographing optical system 30 in accordance with the movement of the subject's eye E. In the present example, the controller 210A is employed as the controller 210, and the data processor 230A is employed as the data processor 230. In FIG. 4F, the illustration of the main controller 211 and the memory 212 is omitted.

The controller 210A includes the tracking controller 213. For example, the tracking controller 213 is included in the main controller 211. The tracking controller 213 is configured to execute control for tracking.

The data processor 230A includes the tracking analyzer 232 in addition to the search processor 231. The search processor 231 may have any one of the configurations of the search processor 231A shown in FIG. 4B, the search processor 231B shown in FIG. 4C, the search processor 231C shown in FIG. 4D, the search processor 231D shown in FIG. 4E, and others. The tracking analyzer 232 is configured to execute data analysis for tracking.

Tracking that may be performed in the present example will be described. Tracking is typically performed with reference to an observation image of the subject's eye E (e.g., an observation image of the fundus Ef or the anterior eye segment). Since the observation image is a moving image, it may be used to grasp the movement of the subject's eye E. Here, the movement of the subject's eye E is the chronological change in the position and orientation of the subject's eye E. In the present example, the fundus Ef is illuminated with near infrared light by the illumination optical system 10, the fundus Ef illuminated with the near infrared light is repeatedly digitally photographed by the photographing optical system 30, and tracking is performed with reference to the near infrared observation image obtained by the repetitive digital photography.

The ophthalmologic apparatus 1 of the present example performs tracking by controlling the movement mechanism 150 based on the observation image obtained by the photographing optical system 30. More specifically, for example, the tracking analyzer 232 may be configured to perform the following processes for the frames sequentially acquired as the observation image: a process of detecting a feature point by analyzing the latest frame; a process of recording the position of the feature point in the latest frame (here, the position may be represented by the x-coordinate and the y-coordinate, or by the coordinates in the two dimensional image space corresponding the x-coordinate and the y-coordinate); and a process of calculating the difference between the latest feature point position and the feature point position obtained before the latest one (e.g., the difference between the latest feature point position and the feature point position acquired immediately before the latest one). The difference between the feature point positions corresponds to the change in the position (positional difference) of the fundus Ef between two imaging times corresponding to the two compared frames. The positional difference information thus obtained is sent to the tracking controller 213. Each time the positional difference information is input from the tracking analyzer 232, the tracking controller 213 executes control of the movement mechanism 150 to move the fundus camera unit 2 in a direction corresponding to the positional difference and by a distance corresponding to the positional difference. In this way, the fundus camera unit 2 may be moved to follow the movement of the subject's eye E.

Another processing example of tracking will be described. For the frames acquired sequentially as an observation image, the tracking analyzer 232 of the present example applies a known image correlation (e.g., phase only correlation) to the latest frame and a frame obtained before the latest one (e.g., the frame obtained immediately before the latest one) to calculate the positional difference between the two frames. The positional difference information thus obtained is sent to the tracking controller 213. Each time the positional difference information is input from the tracking analyzer 232, the tracking controller 213 controls the movement mechanism 150 to move the fundus camera unit 2 in a direction corresponding to the positional difference and by a distance corresponding to the positional difference. In this way, the fundus camera unit 2 may be moved to follow the movement of the subject's eye E.

<User Interface 240>

The user interface 240 includes the display device 241 and the operation device 242. The display device 241 includes the display device 3. The operation device 242 includes various kinds of operation devices and input devices. The user interface 240 may include, for example, a device such as a touch panel (touch screen) in which a display function and an operation function are integrated. It is also possible to employ embodiment examples that do not include at least part of the user interface 240. For example, the display device may be an external device (peripheral equipment) connected to the ophthalmologic apparatus of such an embodiment example.

<Operation>

Some examples of the operation (interested region search) of the ophthalmologic apparatus 1 will be described. It is assumed that preparatory processes similar to those in conventional cases have already been performed. Examples of such preparatory processes include patient ID input, fixation target presentation, fixation position adjustment, alignment, and focus adjustment. The interested region search may be performed at an arbitrary timing after the timing at which the acquisition of the observation image of the fundus Ef may be performed. Typically, the interested region search may be performed within a period of time between the completion of the alignment and the focus adjustment for the fundus Ef and the commencement of the processing using a search result of the interested region.

<First Operation Example>

Figure 6:
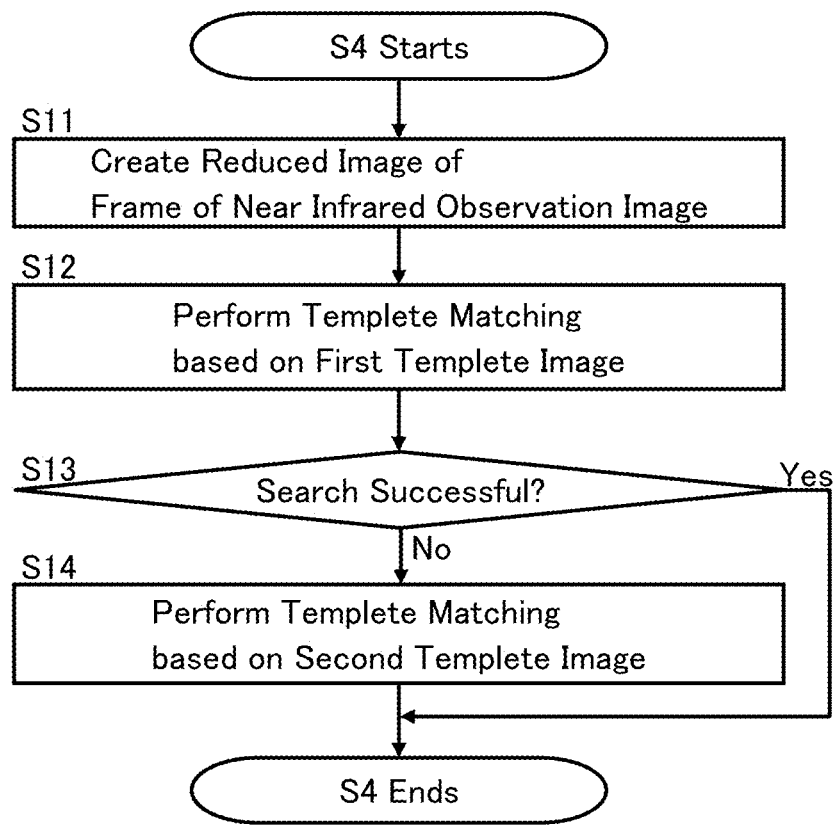
FIG. 6 is a flowchart illustrating an example of the operation of the ophthalmologic apparatus according to some embodiment examples.
Figure 7A:
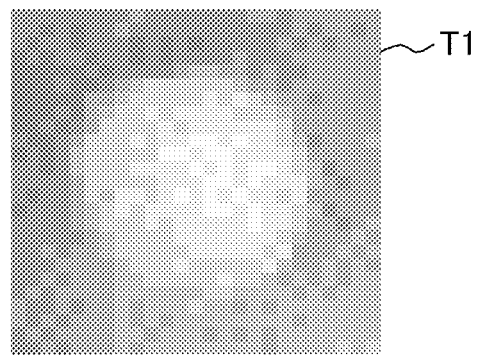
FIG. 7A is a schematic diagram for describing an example of the operation of the ophthalmologic apparatus according to some embodiment examples.
Figure 7B:
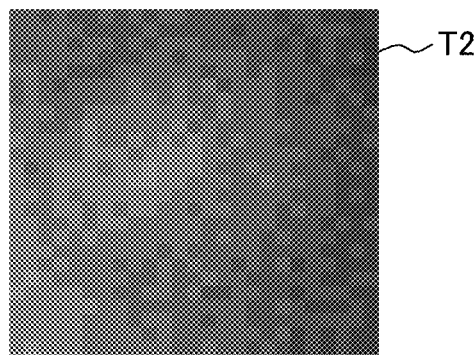
FIG. 7B is a schematic diagram for describing an example of the operation of the ophthalmologic apparatus according to some embodiment examples.
Figure 8:
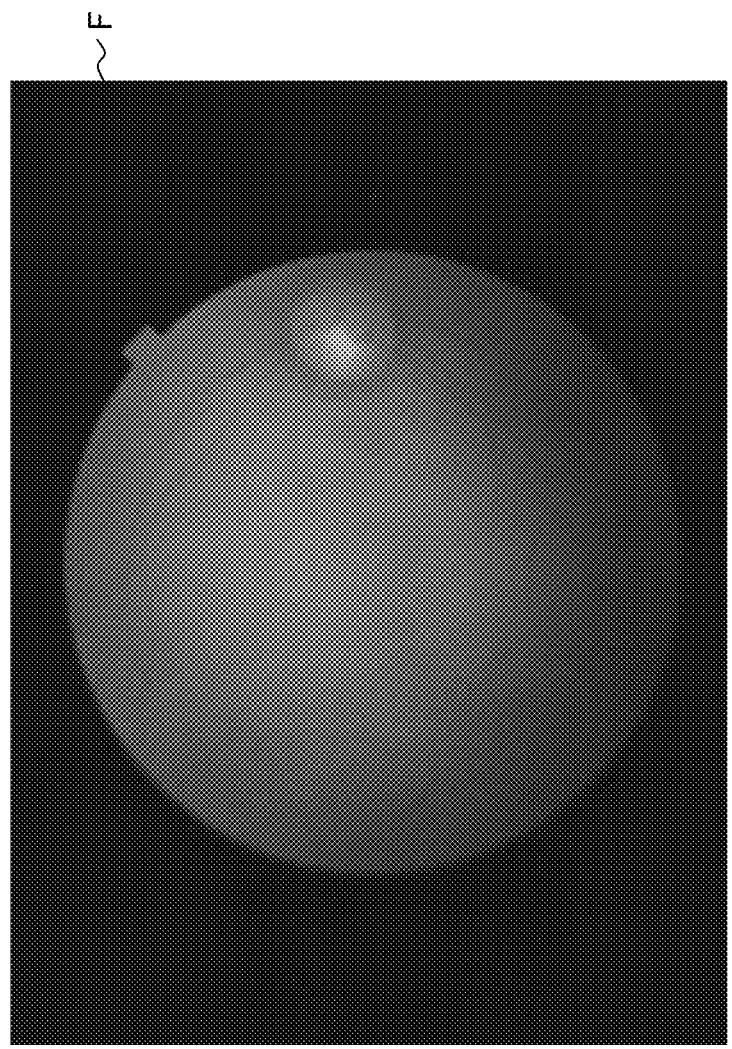
FIG. 8 is a schematic diagram for describing an example of the operation of the ophthalmologic apparatus according to some embodiment examples.
Figure 9:
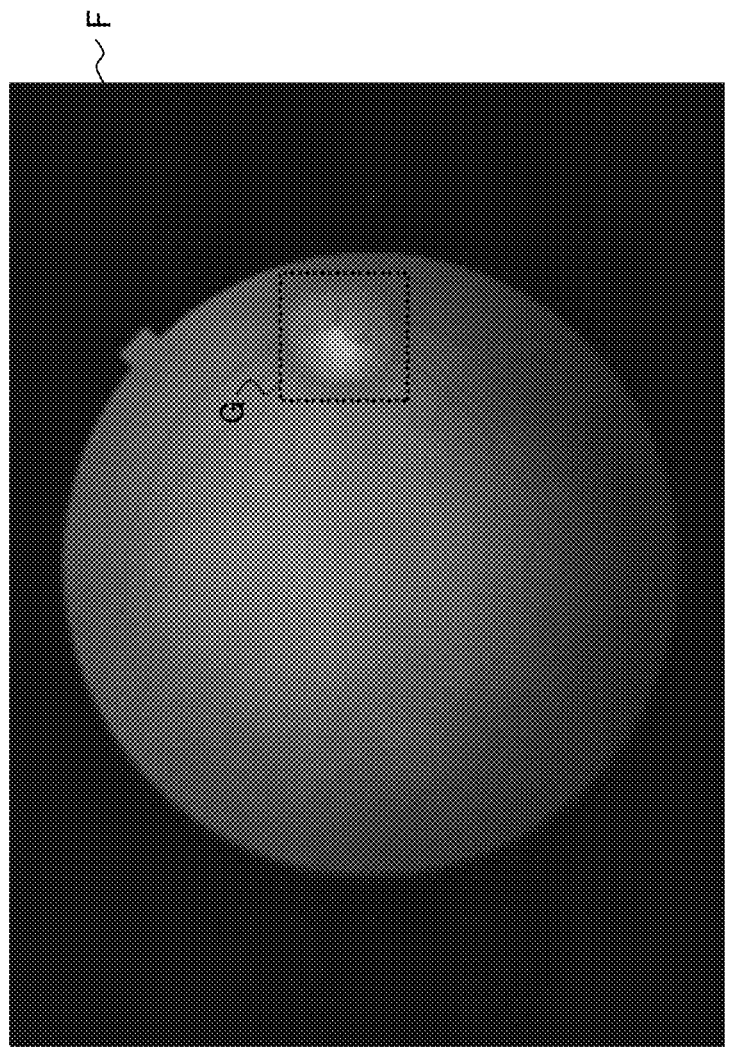
FIG. 9 is a schematic diagram for describing an example of the operation of the ophthalmologic apparatus according to some embodiment examples.

The first example of the operation of the ophthalmologic apparatus 1 will be described with referring to FIG. 5 to FIG. 9. The search processor 231 of the present example is the search processor 231A shown in FIG. 4B. The flowchart of FIG. 5 shows a series of processes performed in the interested region search of the present operation example. The flowchart of FIG. 6 shows a series of processes executable in the step S4 of FIG. 5. FIG. 7A shows a template image that may be used in the step S12 of FIG. 6. FIG. 7B shows a template image that may be used in the step S14 of FIG. 6. Here, the template image of FIG. 7A is the first template image corresponding to the optic nerve head of the persons who are Mongoloid in race. The template image of FIG. 7B is the second template image corresponding to the optic nerve head of the persons who are Caucasian in race. The first template image and the second template image are created in advance and pre-stored in the second search processor 2312 (or in the memory 212, etc.). FIG. 8 shows an example of a front image to which the processing of FIG. 5 is applied. FIG. 9 is referred to for describing the result obtained by applying the processing of FIG. 5 to the front image of FIG. 8.

(S1: Start Capturing of Near Infrared Observation Image)

The interested region search of the present example begins with the acquisition of a front image of the fundus Ef. The front image in the present example is a frame of a near infrared observation image obtained using the illumination optical system 10 and the photographing optical system 30 (see FIG. 8). For example, the front images acquired sequentially (the frames F of the near infrared observation image) are transferred to the memory 212 in a sequential manner by the main controller 211 and temporarily stored in the memory 212, and also supplied to the search processor 231 in a sequential manner.

In the case where the ophthalmologic apparatus 1 of the present example is configured to use a near infrared observation image in at least part of the preparatory processing (e.g., alignment, focus adjustment), the acquisition of the near infrared observation image has already been started, and the capturing of the near infrared observation image (i.e., processing of storing frames of a moving image) for the interest region search starts in the present step. The same applies to the case where the acquisition of the near infrared observation image has started at a stage before the present step.

On the other hand, in the case where the acquisition of a near infrared observation image has not started at a stage before the present step, both the acquisition and the capturing of the near infrared observation image start in the present step.

Further, in the case where the tracking controller 213 and the tracking analyzer 232 are provided as shown in FIG. 4F, tracking may be started at an arbitrary timing after the acquisition of the near infrared observation image has started. Typically, tracking begins after the completion of alignment and focus adjustment.

(S2: Interested Region Search Based on Brightness Variation)

In the present example, the main controller 211 first activates the first search processor 2311. The first search processor 2311 applies the interested region search based on the brightness variation to the frame F of the near infrared observation image captured in the step S1. The interested region search is performed in the manner described above.

(S3: Search Successful?)

If the interested region has been detected by the interested region search in the step S2 (S3: Yes), the processing proceeds to the step S5. On the other hand, if the interested region has not been detected by the interested region search in the step S2 (S3: No), the processing proceeds to the step S4.

(S4: Interested Region Search by Template Matching)

When the interested region has not been detected by the interested region search in the step S2 (S3: No), the main controller 211 activates the second search processor 2312. The second search processor 2312 applies the interested region search by template matching to the frame F of the near infrared observation image captured in the step S1. The interested region search is performed in the manner described above.

Note that the present example assumes that the interested region is detected by the interested region search in the step S4. In the event that the interested region has not been detected in the interested region search in the step S4, for example, the main controller 211 may control the user interface 240 to output a warning, a notice, or the like.

(S5: Record Interested Region Information)

In the event that the interested region has been detected from the frame F by the interested region search in the step S2 or the interested region search in the step S4, the search processor 231A generates interested region information.

The interested region information includes information of predetermined items relating to the detected interested region. For example, the interested region information may include information indicating the position of the interested region, or an image of the interested region and its vicinity. The former and the latter are referred to as interested region position information and an interested region image, respectively.

The interested region position information may include, for example, coordinate information indicating a corresponding area or a feature point of the interested region in the frame F. For example, the area is a periphery of the optic nerve head, and the feature point is the center of the optic nerve head. The coordinate information may be referred to, for example, in the process of applying the interested region search to a frame captured after the frame F.

For example, the interested region image represents at least part of the interested region detected from the frame F and its vicinity. The image region indicated by the reference symbol G in FIG. 9 is an example of the interested region image, and represents the optic nerve head (the interested region) and its vicinity. The interested region image may be used as, for example, a template image in the process of applying the interested region search by template matching to a frame captured after the frame F.

Next, an example of processing performed in the interested region search by template matching in the step S4 will be described with referring to FIG. 6. The present example includes both the use of reduced images (the step S11) and the use of two or more template images (the steps S12 to S14). On the other hand, the interested region search by template matching of another example may include only one of the two, may include none of the two, or may include processing other than the two.

(S11: Create Reduced Image of Frame of Near Infrared Observation Image)

The second search processor 2312 creates a reduced image of the frame F of the near infrared observation image captured in the step S1. The size of the reduced image is, for example, one sixteenth (1/16) the size of the frame F.

(S12: Perform Template Matching Based on First Template Image)

Next, the second search processor 2312 searches for an interested region in the reduced image by applying template matching based on the first template image to the reduced image created in the step S11.

(S13: Search Successful?)

If the interested region has been detected by the template matching in the step S12 (S13: Yes), the processing proceeds to the step S5. On the other hand, if the interested region has not been detected by the template matching in the step S12 (S13: No), the processing proceeds to the step S14.

(S14: Perform Template Matching Based on Second Template Image)

When the interested region has not been detected by the template matching in the step S12 (S13: No), the second search processor 2312 searches for the interested region in the reduced image by applying template matching based on the second template image to the reduced image created in the step S11.

As described above, the present example assumes that an interested region is detected by the interested region search in the step S4. In the event that the interested region has not been detected even in the interested region search in the step S14, for example, the main controller 211 controls the user interface 240 to output a warning, a notice, or the like. When the interested region has been detected in the interested region search in the step S14, the processing proceeds to the step S5.

<Second Operation Example>

Figure 10:
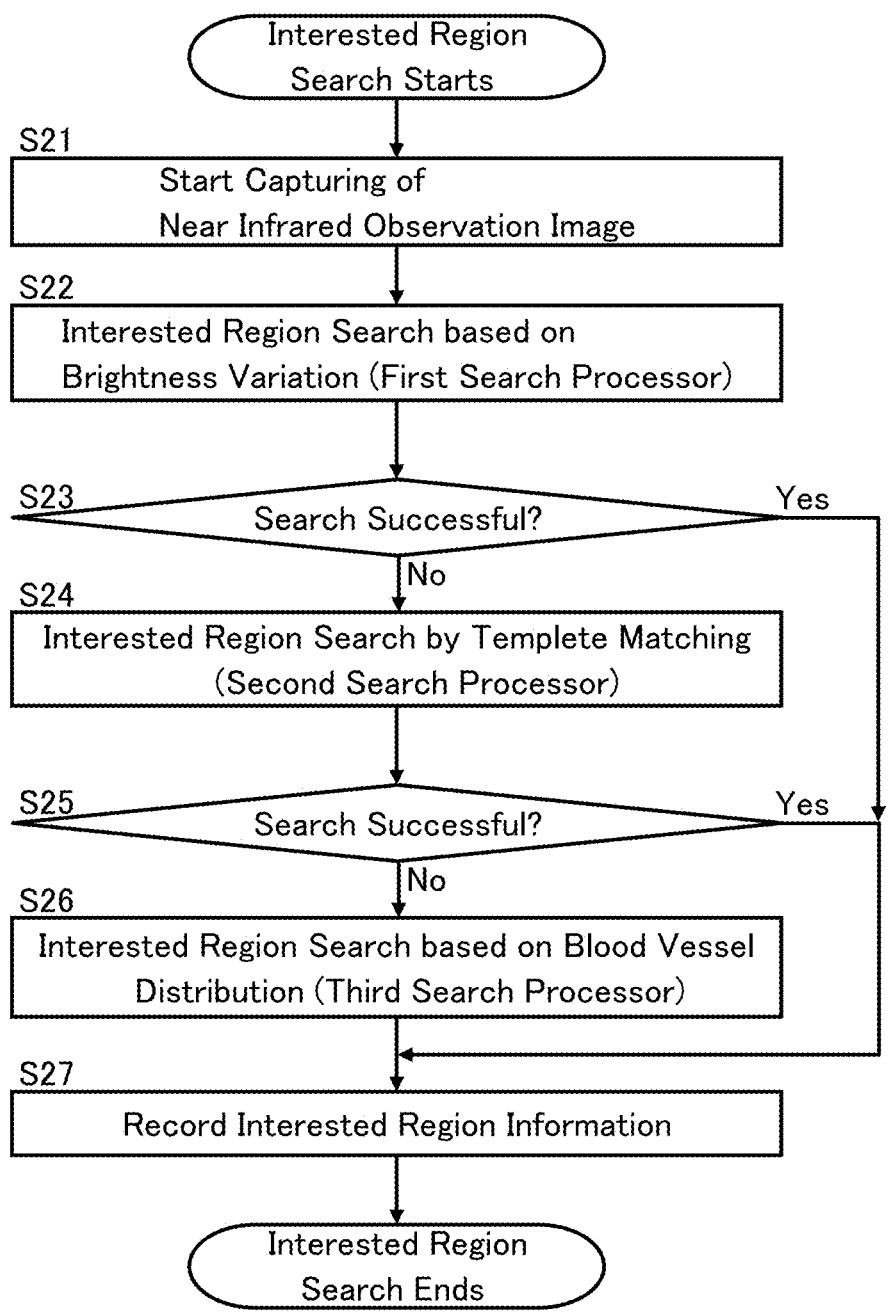
FIG. 10 is a flowchart illustrating an example of the operation of the ophthalmologic apparatus according to some embodiment examples.

The second example of the operation of the ophthalmologic apparatus 1 will be described with referring to FIG. 10. The search processor 231 of the present example is the search processor 231B shown in FIG. 4C.

(S21 to S24)

The steps S21 to S24 are performed in the same manner as the steps S1 to S4 of the first operation example, respectively. In addition, when the interested region has been detected by the interested region search in the step S22 (S23: Yes), the processing proceeds to the step S27.

The present example assumes both the case where an interested region is detected by the interested region search in the step S14 and the case where the interested region is not detected.

(S25: Search Successful?)

If the interested region has been detected by the interested region search in the step S24 (S25: Yes), the processing proceeds to the step S27. On the other hand, if the interested region has not been detected by the interested region search in the step S24 (S25: No), the processing proceeds to the step S26.

(S26: Interested Region Search Based on Blood Vessel Distribution)

When the interested region has not been detected by the interested region search in the step S24 (S25: No), the main controller 211 activates the third search processor 2313. The third search processor 2313 applies the interested region search based on blood vessel distribution to the frame of the near infrared observation image captured in the step S21. The interested region search based on blood vessel distribution is performed in the manner described above.

The present example assumes that the interested region is detected by the interested region search in the step S26. In the event that the interested region has not been detected even in the interested region search in the step S26, for example, the main controller 211 controls the user interface 240 to output a warning, a notice, or the like.

(S27: Record Interested Region Information)

When the interested region has been detected from the frame captured in the step S21 by the interested region search in the step S22, the interested region search in the step S24, or the interested region search in the step S26, the search processor 231B generates interested region information. The process of generating the interested region information is performed in the same manner as the step S5 of the first operation example.

<Third Operation Example>

Figure 11:
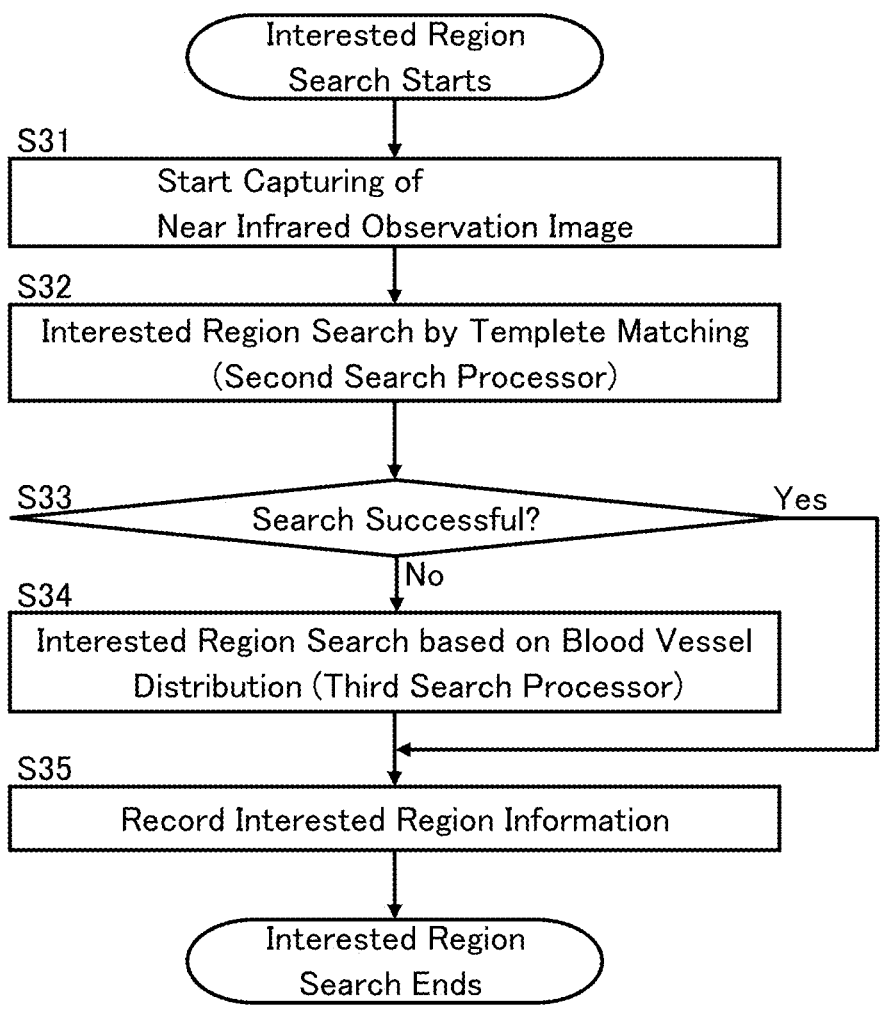
FIG. 11 is a flowchart illustrating an example of the operation of the ophthalmologic apparatus according to some embodiment examples.

The third example of the operation of the ophthalmologic apparatus 1 will be described with referring to FIG. 11. The search processor 231 of the present example is the search processor 231C shown in FIG. 4D.

(S31: Start Capturing Near Infrared Observation Image)

First, the ophthalmologic apparatus 1 starts capturing of a near infrared observation image and feeds a frame thereof into the search processor 231C in the same manner as the step S1 of the first operation example.

(S32 to S34)

The steps S32 to S34 are performed in the same manner as the steps S24 to S26 of the second operation example, respectively. In addition, if the interested region has been detected by the interested region search of the step S32 (S33: Yes), the processing proceeds to the step S35.

(S35: Record Interested Region Information)

When the interested region search in the step S32 or the interested region search in the step S34 has detected the interested region from the frame captured in the step S31, the search processor 231C generates interested region information. The process of generating the interested region information is performed in the same manner as the step S5 of the first operation example.

<Fourth Operation Example>

Figure 12:
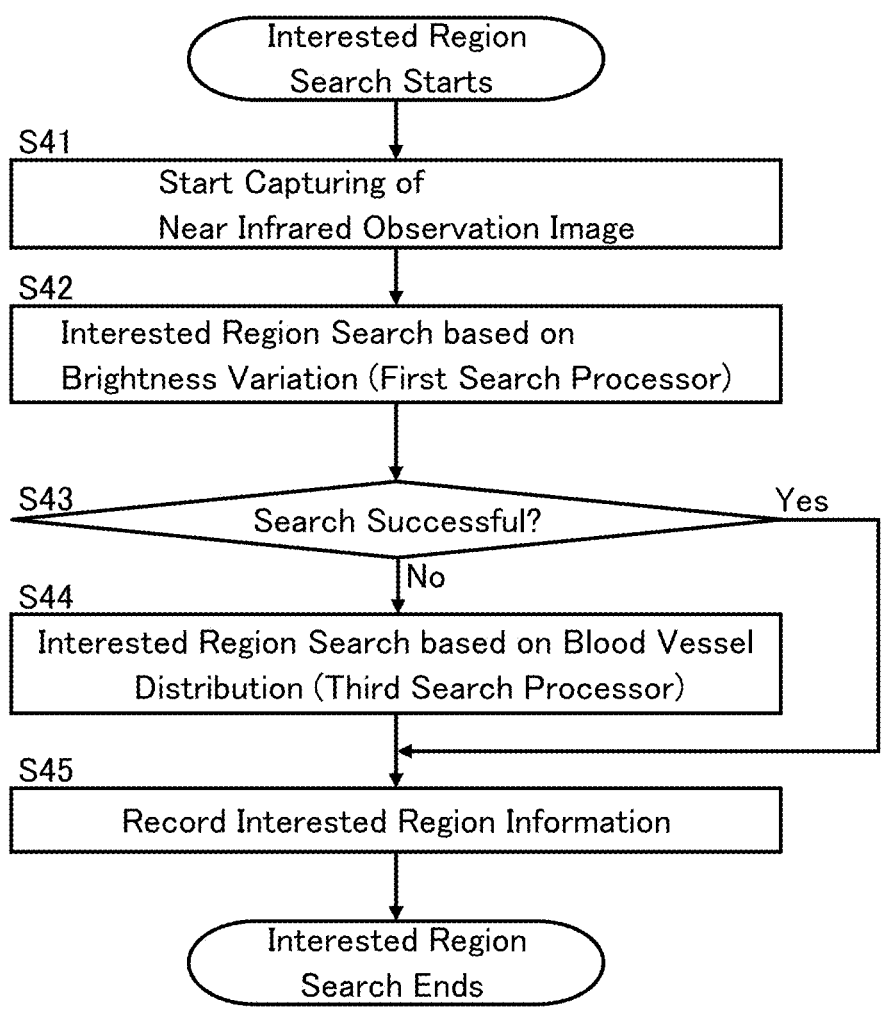
FIG. 12 is a flowchart illustrating an example of the operation of the ophthalmologic apparatus according to some embodiment examples.

The fourth example of the operation of the ophthalmologic apparatus 1 will be described with referring to FIG. 12. The search processor 231 of the present example is the search processor 231D shown in FIG. 4E.

(S41: Start Capturing Near Infrared Observation Image)

First, the ophthalmologic apparatus 1 starts capturing of a near infrared observation image and feeds a frame thereof into the search processor 231D in the same manner as the step S1 of the first operation example.

(S42 to S43)

The steps S42 to S43 are performed in the same manner as the steps S2 to S3 of the first operation example, respectively. In addition, if the interested region has been detected by the interested region search of the step S42 (S43: Yes), the processing proceeds to the step S45. On the other hand, if the interested region has not been detected by the interested region search in the step S42 (S43: No), the processing proceeds to the step S44.

(S44: Interested Region Search Based on Blood Vessel Distribution)

When the interested region has not been detected by the interested region search in the step S42 (S43: No), the main controller 211 activates the third search processor 2313. The third search processor 2313 applies the interested region search based on blood vessel distribution to the frame of the near infrared observation image captured in the step S41. The interested region search is performed in the manner as the step S26 of the second operation example.

The present example assumes that the interested region is detected by the interested region search in the step S44. In the event that the interested region has not been detected in the interested region search in the step S44, for example, the main controller 211 controls the user interface 240 to output a warning, a notice, or the like.

(S45: Record Interested Region Information)

When the interested region search in the step S42 or the interested region search in the step S44 has detected the interested region from the frame captured in the step S41, the search processor 231D generates interested region information. The process of generating the interested region information is performed in the same manner as the step S5 of the first operation example.

<Actions and Effects>

Some actions and effects of some embodiment examples will be described.

The ophthalmologic apparatus (1) according to some embodiment examples may include a front image acquiring device, a first search processor, and a second search processor (see FIG. 4B).

The front image acquiring device is configured to acquire a front image of the fundus of the subject's eye. In the exemplary ophthalmologic apparatus 1, the front image acquiring device includes the illumination optical system 10 and the photographing optical system 30. While the exemplary ophthalmologic apparatus 1 acquires a front image by photographing the fundus Ef, the exemplary ophthalmologic apparatus may be configured to receive a front image from a different apparatus or device, or from a storage device or a memory. In the case that a front image is acquired from a different apparatus, a storage device, or the like, the front image acquiring device of the exemplary ophthalmologic apparatus 1 includes the communication device or the drive device described above.

The first search processor is configured to search for an interested region corresponding to an interested site of the fundus based on a brightness variation in the front image acquired by the front image acquiring device. The first search processor of the exemplary ophthalmologic apparatus 1 includes the first search processor 2311.

The second search processor is configured to search for the interested region by template matching between the front image and a template image in the event that the interested region has not been detected by the first search processor.

According to the ophthalmologic apparatus as described above, the reliability of interested site detection from the front image may be improved and the efficiency of the entire processing may be improved, by applying the two image processing methods (techniques) in a step by step manner.

The ophthalmologic apparatus (1) according to some embodiment examples may further include a third search processor (see FIG. 4C). The third search processor is configured to detect a blood vessel region corresponding to a blood vessel of the fundus by analyzing the front image, and then search for the interested region based on a distribution of the blood vessel region detected, in the event that the interested region has not been detected by the second search processor.

According to the ophthalmologic apparatus as described above, the reliability of interested site detection from the front image may be improved and the efficiency of the entire processing may be improved, by applying the three image processing methods (techniques) in a step by step manner.

The ophthalmologic apparatus (1) according to some embodiment examples may include a front image acquiring device, a second search processor, and a third search processor (see FIG. 4D). According to such an ophthalmologic apparatus, the reliability of interested site detection from the front image may be improved and the efficiency of the entire processing may be improved, by applying the two image processing methods (techniques) in a step by step manner.

The ophthalmologic apparatus (1) according to some embodiment examples may include a front image acquiring device, a first search processor, and a third search processor (see FIG. 4E). According to such an ophthalmologic apparatus, the reliability of interested site detection from the front image may be improved and the efficiency of the entire processing may be improved, by applying the two image processing methods (techniques) in a step by step manner.

In some embodiment examples, the size of the template image may be smaller than the size of the fundus front image. If this is the case, the second search processor is configured to create a reduced image of a size corresponding to the size of the template image by resizing the front image, and search for the interested region by applying template matching based on the template image to the reduced image. Here, the reduction ratio for creating the reduced image from the front image may be a default value or a value set based on the size of the front image and/or the size of the template image.

According to such an ophthalmologic apparatus, the influence of individual differences in the size of the interested site on the interested region search may be lessened. Furthermore, the computational resources required for template matching may be reduced.

In some embodiment examples, the second search processor may pre-store two or more template images respectively corresponding to two or more attributes. Further, the second search processor may be configured to search for the interested region by template matching between each of the two or more template images and the front image.

According to such an ophthalmologic apparatus, it is possible to improve the reliability of interested site detection from the front image of the fundi of subject's eyes having various attributes.

In some embodiment examples, the interested region may include an optic nerve head region corresponding to the optic nerve head, and the template image may be an image of the optic nerve head and its vicinity.

With this, it is possible to improve the reliability of the detection of the optic nerve head that is one of main interested sites of eye fundi.

In some embodiment examples, the interested region may include an optic nerve head region corresponding to the optic nerve head. In addition, the first search processor may be configured to search for a boundary of the optic nerve head region by a process of identifying a location in the front image of the fundus in which the brightness variation is discontinuous.

According to such an ophthalmologic apparatus, edge detection may be performed in the interested region search based on the brightness variation executed by the first search processor. With this, the edge of the optic nerve head may be detected with high reliability.

In some embodiment examples, the interested region may include an optic nerve head region corresponding to the optic nerve head. In addition, the third search processor may be configured to search for the optic nerve head region based on one or more parameters among the width, the density and the orientation of the blood vessel region.

According to such an ophthalmologic apparatus, the third search processor may detect the optic nerve head with high reliability by referring to the distribution of the blood vessels in the fundus.

In some embodiment examples, the front image acquiring device may be configured to further acquire another front image of the fundus, wherein the another front image is acquired by a modality different from the modality that acquires the front image of the fundus. Here, both of the front images may be photographed or imaged by the ophthalmologic apparatus 1, only one of the front images may be photographed or imaged by the ophthalmologic apparatus 1, or both of the front images may be input from the outside.

In addition, the third search processor may be configured to perform the following series of processes. First, the third search processor detects the first blood vessel region corresponding to a blood vessel of the fundus by analyzing the another front image. Next, the third search processor performs registration between the front image and the another front image. Subsequently, the third search processor identifies the second blood vessel region in the front image corresponding to the first blood vessel region, based on the result of the registration. Finally, the third search processor searches for the interested region based on a distribution of the second blood vessel region.

According to such an ophthalmologic apparatus, the third search processor may obtain the blood vessel distribution in the front image with reference to the blood vessel distribution obtained from the another front image. Therefore, the reliability of interested site detection may be improved.

Similarly, in some embodiment examples capable of further acquiring another front image of the fundus acquired by a modality different from the modality that acquires the front image of the fundus, the third search processor may be configured to perform the following series of processes. First, the third search processor detects a blood vessel region corresponding to a blood vessel of the fundus by analyzing the another front image. Next, the third search processor searches for the first interested region based on a distribution of the blood vessel region detected from the another front image. Subsequently, the third search processor performs registration between the front image and the another front image. Finally, the third search processor identifies, as the interested region, the second interested region in the front image corresponding to the first interested region, based on the result of the registration.

According to such an ophthalmologic apparatus, the third search processor may detect the interested site in the another front image based on the blood vessel distribution obtained from the another front image, and then detect the interested site in the front image by referring to the interested site in the another front image. Therefore, the reliability of interested site detection may be improved.

In some embodiment examples, the front image of the fundus may be an image obtained by digitally photographing the fundus being illuminated with near infrared light. More specifically, the front image of the fundus may be a frame of a moving image obtained by repeatedly performing digital photography on the fundus being illuminated with near infrared light.

Such an ophthalmologic apparatus serves to improve the reliability of interested site detection from the front image of the fundus acquired using near infrared light, which does not cause dazzling for the subject and does not induce miosis.

In some exemplary ophthalmologic apparatuses capable of acquiring a near infrared moving image, the front image acquiring device may include an illumination system and a photographing system. The illumination system is configured to illuminate the fundus with near infrared light. The photographing system includes an image sensor and is configured to repeatedly perform digital photography of the fundus being illuminated with the near infrared light. In other words, the front image acquiring device may be configured to be capable of performing near infrared eye fundus observation. In addition, the exemplary ophthalmologic apparatus may include a movement mechanism and a movement processor. The moving mechanism is configured to move the illumination system and the photographing system. The movement processor is configured to control the movement mechanism based on a moving image obtained by the photographing system.

The illumination system of the exemplary ophthalmologic apparatus 1 includes at least the illumination optical system 10. The illumination system of the exemplary ophthalmologic apparatus 1 may further include an element for controlling an element of the illumination optical system 10, and/or an element for driving an element of the illumination optical system 10. The photographing system of the exemplary ophthalmologic apparatus 1 includes at least the photographing optical system 30. The photographing system of the exemplary ophthalmologic apparatus 1 may further include an element for controlling an element of the photographing optical system 30, and/or an element for driving an element of the photographing optical system 30. The movement mechanism of the exemplary ophthalmologic apparatus 1 includes the movement mechanism 150. Further, the movement processor of the exemplary ophthalmologic apparatus 1 includes the tracking controller 213 and the tracking analyzer 232 (see FIG. 6F).

Some embodiment examples provide a method of controlling an ophthalmologic apparatus. An ophthalmologic apparatus to which the control method may be applied includes a processor configured to process a front image of a fundus of a subject's eye. Such a processor of the exemplary ophthalmologic apparatus 1 includes at least the search processor 231.

The first aspect of the control method of some embodiment examples includes the first search control step and the second search control step. The first search control step causes the processor to perform a process of searching for an interested region corresponding to an interested site of the fundus based on a brightness variation in the front image of the fundus. The second search control step causes the processor to perform a process of searching for the interested region by template matching between the front image and a template image, in the event that the interested region has not been detected by the process performed in the first search control step.

The first aspect of the control method of some embodiment examples may further include the third search control step. The third search control step causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the second search control step.

The second aspect of the control method of some embodiment examples includes the second search control step and the third search control step. The second search control step causes the processor to perform a process of searching for an interested region by template matching between the front image of the fundus and a template image. The third search control step causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the second search control step.

The third aspect of the control method of some embodiment examples includes the first search control step and the third search control step. The first search control step causes the processor to perform a process of searching for an interested region corresponding to an interested site of the fundus based on a brightness variation in the front image of the fundus. The third search control step causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the first search control step.

Any of the matters or items described for the exemplary ophthalmologic apparatus 1 may be combined with any of the control methods of the exemplary ophthalmologic apparatus.

Some embodiment examples provide a program configured to cause an ophthalmologic apparatus to perform any of the exemplary control methods. Any of the matters or items described in some embodiment examples may be combined with the program.

Further, it is possible to create a computer-readable non-transitory recording medium storing the program described above. Any of the matters or items described in some embodiment examples may be combined with the recording medium. The non-transitory recording medium may have any form, and examples thereof include a magnetic disk, an optical disk, a magneto-optical disk, a semiconductor memory, and the like.

According to the method, the program, or the recording medium according to some embodiment examples, it is possible to improve the reliability of interested site detection from the front image by applying two or more image processing methods in a step by step manner. In addition, the efficiency of the entire processing may be improved. Furthermore, actions and effects are exhibited according to matters or items combined with the method, the program, or the recording medium according to some embodiment examples.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What we claim is:

1. An ophthalmologic apparatus comprising:
    a front image acquiring device configured to acquire a front image of a fundus of a subject's eye;
    a first search processor configured to search for an interested region corresponding to an interested site of the fundus based on a brightness variation in the front image; and
    a second search processor configured to search for the interested region by template matching between the front image and a template image in the event that the interested region has not been detected by the first search processor.

2. The ophthalmologic apparatus of claim 1, further comprising a third search processor configured to detect a blood vessel region corresponding to a blood vessel of the fundus by analyzing the front image and search for the interested region based on a distribution of the blood vessel region in the event that the interested region has not been detected by the second search processor.

3. An ophthalmologic apparatus comprising:
a front image acquiring device configured to acquire a front image of a fundus of a subject's eye;
a second search processor configured to search for an interested region by template matching between the front image and a template image; and
a third search processor configured to detect a blood vessel region corresponding to a blood vessel of the fundus by analyzing the front image and search for the interested region based on a distribution of the blood vessel region in the event that the interested region has not been detected by the second search processor.

4. An ophthalmologic apparatus comprising:
a front image acquiring device configured to acquire a front image of a fundus of a subject's eye;
a first search processor configured to search for an interested region corresponding to an interested site of the fundus based on a brightness variation in the front image; and
a third search processor configured to detect a blood vessel region corresponding to a blood vessel of the fundus by analyzing the front image and search for the interested region based on a distribution of the blood vessel region in the event that the interested region has not been detected by the first search processor.

5. The ophthalmologic apparatus of claim 1, wherein
a size of the template image is smaller than a size of the front image, and
the second search processor is configured to create a reduced image of a size corresponding to the size of the template image by resizing the front image, and search for the interested region by applying template matching based on the template image to the reduced image.

6. The ophthalmologic apparatus of claim 1, wherein the second search processor is configured to pre-store two or more template images respectively corresponding to two or more attributes, and search for the interested region by template matching between each of the two or more template images and the front image.

7. The ophthalmologic apparatus of claim 1, wherein
the interested region includes an optic nerve head region corresponding to an optic nerve head of the fundus, and
the template image is an image of the optic nerve head and vicinity thereof.

8. The ophthalmologic apparatus of claim 1, wherein
the interested region includes an optic nerve head region corresponding to an optic nerve head of the fundus, and
the first search processor is configured to search for a boundary of the optic nerve head region by identifying a location in the front image in which a brightness variation is discontinuous.

9. The ophthalmologic apparatus of claim 3, wherein
the front image acquiring device is configured to acquire another front image of the fundus acquired using a modality different from a modality used for acquisition of the front image, and
the third search processor is configured to detect a blood vessel region corresponding to a blood vessel of the fundus by analyzing the another front image, search for a first interested region based on a distribution of the blood vessel region detected from the another front image, perform registration between the front image and the another front image, and identify, as the interested region, a second interested region of the front image corresponding to the first interested region based on a result of the registration.

10. The ophthalmologic apparatus of claim 4, wherein
the front image acquiring device is configured to acquire another front image of the fundus acquired using a modality different from a modality used for acquisition of the front image, and
the third search processor is configured to detect a blood vessel region corresponding to a blood vessel of the fundus by analyzing the another front image, search for a first interested region based on a distribution of the blood vessel region detected from the another front image, perform registration between the front image and the another front image, and identify, as the interested region, a second interested region of the front image corresponding to the first interested region based on a result of the registration.

11. The ophthalmologic apparatus of claim 1, wherein the front image is obtained by digitally photographing the fundus illuminated with near infrared light.

12. A method of controlling an ophthalmologic apparatus that includes a processor configured to process a front image of a fundus of a subject's eye, the method comprising:
a first search control step that causes the processor to perform a process of searching for an interested region corresponding to an interested site of the fundus based on a brightness variation in the front image; and
a second search control step that causes the processor to perform a process of searching for the interested region by template matching between the front image and a template image in the event that the interested region has not been detected by the process performed in the first search control step.

13. The control method of claim 12, further comprising a third search control step that causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the second search control step.

14. A method of controlling an ophthalmologic apparatus that includes a processor configured to process a front image of a fundus of a subject's eye, the method comprising:
a second search control step that causes the processor to perform a process of searching for an interested region by template matching between the front image and a template image; and
a third search control step that causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the second search control step.

15. A method of controlling an ophthalmologic apparatus that includes a processor configured to process a front image of a fundus of a subject's eye, the method comprising:
a first search control step that causes the processor to perform a process of searching for an interested region corresponding to an interested site of the fundus based on a brightness variation in the front image; and a third search control step that causes the processor to perform a process of detecting a blood vessel region corresponding to a blood vessel of the fundus by analyzing the front image, and a process of searching for the interested region based on a distribution of the blood vessel region, in the event that the interested region has not been detected by the process performed in the first search control step.

* * * * *